US012805793B2

(12) United States Patent
Forsyth et al.

(10) Patent No.: US 12,805,793 B2
(45) Date of Patent: Nov. 24, 2026

(54) PROCESSING RADIO FREQUENCY WIRELESS SIGNALS IN A MOTION DETECTION SYSTEM

(71) Applicant: Cognitive Systems Corp., Waterloo (CA)

(72) Inventors: Amanda Forsyth, Waterloo (CA); Colin Brennan, Waterloo (CA); Sarmina Manku, Waterloo (CA)

(73) Assignee: Cognitive Systems Corp., Waterloo (CA)

( * ) Notice: Subject to any disclaimer, the term of this patent is extended or adjusted under 35 U.S.C. 154(b) by 40 days.

(21) Appl. No.: 18/468,457

(22) Filed: Sep. 15, 2023

(65) Prior Publication Data

US 2024/0000376 A1 Jan. 4, 2024

Related U.S. Application Data

(63) Continuation-in-part of application No. PCT/CA2022/050228, filed on Feb. 17, 2022, which (Continued)

(51) Int. Cl.

*A61B 5/00* (2006.01)
*A61B 5/11* (2006.01)

(Continued)

(52) U.S. Cl.

CPC .......... *A61B 5/4815* (2013.01); *A61B 5/0004* (2013.01); *A61B 5/1118* (2013.01);

(Continued)

(58) Field of Classification Search

None

See application file for complete search history.

(56) References Cited

U.S. PATENT DOCUMENTS 7,009,561 B2 * 3/2006 Menache .............. A63F 13/213 352/53
7,432,810 B2 * 10/2008 Menache .............. G01S 5/0247 156/60

(Continued)

FOREIGN PATENT DOCUMENTS

CN 105592777 5/2016
EP 3695783 8/2020

(Continued)

OTHER PUBLICATIONS

EPO, European Extended Search Report issued in Application No. 22770108.3 on Mar. 21, 2024, 12 pages.

(Continued)

*Primary Examiner* — William L Bashore
*Assistant Examiner* — Koorosh Nehchiri
(74) *Attorney, Agent, or Firm* — Henry Patent Law Firm PLLC

(57) ABSTRACT

In a general aspect, a method of operating a motion detection system includes receiving, by operation of one or more communication interfaces, radio frequency wireless signals communicated by a plurality of wireless communication devices. The radio frequency wireless signals are processed to generate channel information. By operation of a motion detection engine of the motion detection system, generating motion data based on the channel information that includes a series of vectors in a series of time points within the time period. The motion data includes motion indicator values indicative of a degree of motion that occurred in the space and motion localization values for a plurality of locations. Processing the series of vectors includes determining an aggregate degree of motion that occurred at each of the individual locations during the time period and determining (Continued)

a duration of activity that occurred at each of the individual locations during the time period.

12 Claims, 25 Drawing Sheets

Related U.S. Application Data is a continuation of application No. 17/201,724, filed on Mar. 15, 2021, now abandoned.

(51) Int. Cl.
*G06F 3/04847* (2022.01)
*G06F 3/14* (2006.01)
*H04W 4/38* (2018.01)

(52) U.S. Cl.
CPC .......... *A61B 5/4809* (2013.01); *A61B 5/7278* (2013.01); *A61B 5/742* (2013.01); *A61B 5/7475* (2013.01); *G06F 3/04847* (2013.01); *G06F 3/14* (2013.01); *H04W 4/38* (2018.02)

(56) References Cited

U.S. PATENT DOCUMENTS

| | | | | |
|---|---|---|---|---|
| 8,660,578 | B1 * | 2/2014 | Yang | G01S 13/003 455/456.3 |
| 8,710,984 | B2 * | 4/2014 | Wilson | G01D 21/00 340/541 |
| 9,523,760 | B1 | 12/2016 | Kravets et al. | |
| 9,524,628 | B1 | 12/2016 | Omer et al. | |
| 9,584,974 | B1 | 2/2017 | Omer et al. | |
| 9,869,759 | B2 | 1/2018 | Furuskog et al. | |
| 9,927,519 | B1 * | 3/2018 | Omer | G08B 13/2491 |
| 9,989,622 | B1 * | 6/2018 | Griesdorf | G01S 13/878 |
| 10,004,076 | B1 | 6/2018 | Griesdorf et al. | |
| 10,048,350 | B1 | 8/2018 | Piao et al. | |
| 10,051,414 | B1 | 8/2018 | Omer et al. | |
| 10,064,014 | B2 * | 8/2018 | Wootton | H04W 4/023 |
| 10,108,903 | B1 | 10/2018 | Piao et al. | |
| 10,109,167 | B1 | 10/2018 | Olekas et al. | |
| 10,109,168 | B1 | 10/2018 | Devison et al. | |
| 10,111,228 | B2 | 10/2018 | Griesdorf et al. | |
| 10,129,853 | B2 | 11/2018 | Manku et al. | |
| 10,199,835 | B2 * | 2/2019 | Leabman | H02J 50/40 |
| 10,228,439 | B1 | 3/2019 | Olekas et al. | |
| 10,264,405 | B1 | 4/2019 | Manku et al. | |
| 10,318,890 | B1 | 6/2019 | Kravets et al. | |
| 10,380,856 | B2 | 8/2019 | Devison et al. | |
| 10,393,866 | B1 | 8/2019 | Kravets et al. | |
| 10,404,387 | B1 | 9/2019 | Devison et al. | |
| 10,438,468 | B2 * | 10/2019 | Olekas | G01S 13/56 |
| 10,459,074 | B1 | 10/2019 | Omer et al. | |
| 10,459,076 | B2 | 10/2019 | Kravets et al. | |
| 10,460,581 | B1 | 10/2019 | Devison et al. | |
| 10,498,467 | B1 | 12/2019 | Ravkine | |
| 10,499,364 | B1 | 12/2019 | Ravkine | |
| 10,506,384 | B1 | 12/2019 | Omer et al. | |
| 10,565,860 | B1 | 2/2020 | Omer et al. | |
| 10,567,914 | B1 | 2/2020 | Omer et al. | |
| 10,600,314 | B1 | 3/2020 | Manku et al. | |
| 10,605,907 | B2 | 3/2020 | Kravets et al. | |
| 10,605,908 | B2 | 3/2020 | Kravets et al. | |
| 10,743,143 | B1 | 8/2020 | Devison et al. | |
| 10,849,006 | B1 | 11/2020 | Beg et al. | |
| 2007/0296571 | A1 * | 12/2007 | Kolen | A61B 5/1113 340/539.11 |
| 2012/0146788 | A1 | 6/2012 | Wilson et al. | |
| 2014/0247179 | A1 | 9/2014 | Furuskog | |
| 2016/0210838 | A1 * | 7/2016 | Yan | G08B 25/001 |
| 2017/0243508 | A1 * | 8/2017 | Cheng | G09B 5/02 |
| 2017/0359804 | A1 | 12/2017 | Manku et al. | |
| 2018/0006438 | A1 | 1/2018 | Fitzgerald | |
| 2018/0064388 | A1 * | 3/2018 | Heneghan | A61B 5/4812 |
| 2018/0270821 | A1 | 9/2018 | Griesdorf et al. | |
| 2019/0052995 | A1 | 2/2019 | Agrawal et al. | |
| 2019/0097865 | A1 | 3/2019 | Xu et al. | |
| 2019/0122514 | A1 | 4/2019 | Olekas et al. | |
| 2019/0146075 | A1 * | 5/2019 | Kravets | G01S 13/762 455/67.11 |
| 2019/0146076 | A1 | 5/2019 | Kravets et al. | |
| 2019/0146077 | A1 | 5/2019 | Kravets et al. | |
| 2019/0147713 | A1 | 5/2019 | Devison et al. | |
| 2019/0170869 | A1 | 6/2019 | Kravets et al. | |
| 2020/0170567 | A1 | 6/2020 | Russell et al. | |
| 2020/0175405 | A1 | 6/2020 | Omer et al. | |
| 2020/0178033 | A1 | 6/2020 | Omer et al. | |
| 2020/0264292 | A1 | 8/2020 | Kravets et al. | |
| 2020/0351576 | A1 | 11/2020 | Beg et al. | |
| 2020/0351692 | A1 | 11/2020 | Beg et al. | |
| 2020/0366386 | A1 | 11/2020 | Bugos et al. | |
| 2022/0287629 | A1 * | 9/2022 | Forsyth | G09G 5/36 |

FOREIGN PATENT DOCUMENTS

| | | |
|---|---|---|
| WO | 2015168700 | 11/2015 |
| WO | 2017106976 | 6/2017 |
| WO | 2017132765 | 8/2017 |
| WO | 2017210770 | 12/2017 |
| WO | 2018094502 | 5/2018 |
| WO | 2019075552 | 4/2019 |
| WO | 2022073112 | 4/2022 |
| WO | 2022192987 | 9/2022 |

OTHER PUBLICATIONS

WIPO, International Search Report and Written Opinion mailed May 16, 2022, in PCT/CA2022/050228, 10 pgs.
USPTO, Final Office Action mailed Jun. 14, 2022, in U.S. Appl. No. 17/201,724, 13 pgs.
USPTO, Non-Final Office Action mailed Jun. 3, 2021, in U.S. Appl. No. 17/201,724, 28 pgs.
USPTO, Non-Final Office Action mailed Mar. 1, 2022, in U.S. Appl. No. 17/201,724, 33 pgs.
USPTO, Final Office Action mailed Sep. 21, 2021, in U.S. Appl. No. 17/201,724, 41 pgs.
EPO, Communication pursuant to Article 94(3) issued in Application No. 22770108.3 on Jan. 30, 2025, 5 pages.
EPO, Communication pursuant to Article 94(3) issued in Application No. 22770108.3 on Nov. 20, 2025, 8 pages.
CNIPA, Office Action issued in Application No. 202280034837.0 on Jul. 30, 2026, 28 pages.

* cited by examiner

PROCESSING RADIO FREQUENCY WIRELESS SIGNALS IN A MOTION DETECTION SYSTEM

CROSS-REFERENCE TO RELATED APPLICATIONS

This application is a continuation-in-part of International Patent Application No. PCT/CA2022/050228, filed on Feb. 17, 2022. International Patent Application No. PCT/CA2022/050228 claims priority to U.S. Non-provisional application Ser. No. 17/201,724 filed on Mar. 15, 2021. International Patent Application No. PCT/CA2022/050228 and U.S. patent application Ser. No. 17/201,724 are each hereby incorporated by reference.

BACKGROUND

The following description relates to processing radio frequency wireless signals in a motion detection system.

Motion detection systems have been used to detect movement, for example, of objects in a room or an outdoor area. In some example motion detection systems, infrared or optical sensors are used to detect movement of objects in the sensor's field of view. Motion detection systems have been used in security systems, automated control systems, and other types of systems.

DETAILED DESCRIPTION

Figure 1:
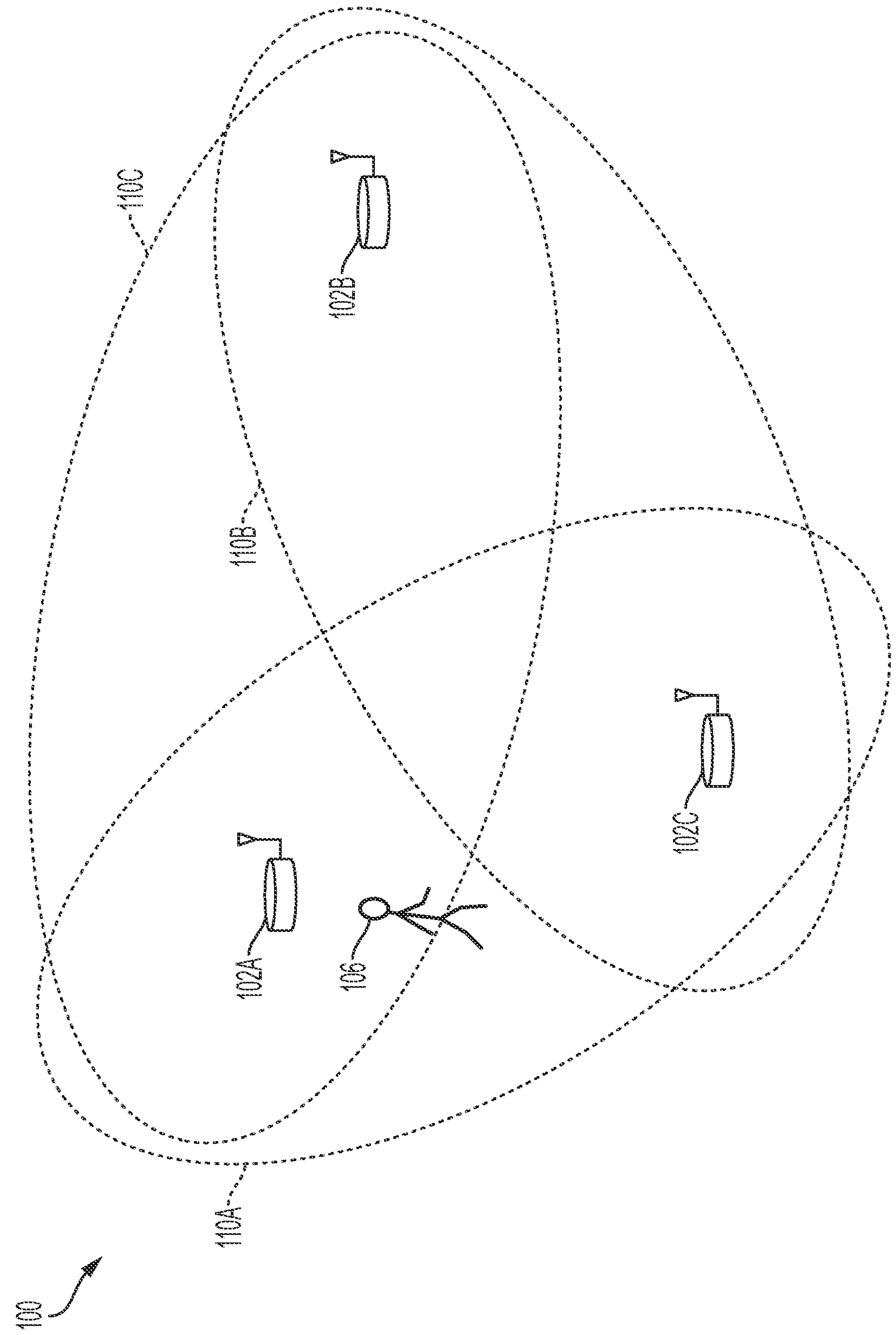
FIG. 1 is a diagram showing an example wireless communication system.

In some aspects of what is described here, a wireless sensing system can process wireless signals (e.g., radio frequency signals) transmitted through a space between wireless communication devices for wireless sensing applications. Example wireless sensing applications include detecting motion, which can include one or more of the following: detecting motion of objects in the space, motion tracking, localization of motion in a space, breathing detection, breathing monitoring, presence detection, gesture detection, gesture recognition, human detection (e.g., moving and stationary human detection), human tracking, fall detection, speed estimation, intrusion detection, walking detection, step counting, respiration rate detection, sleep pattern detection, sleep quality monitoring, apnea estimation, posture change detection, activity recognition, gait rate classification, gesture decoding, sign language recognition, hand tracking, heart rate estimation, breathing rate estimation, room occupancy detection, human dynamics monitoring, and other types of motion detection applications. Other examples of wireless sensing applications include object recognition, speech recognition, keystroke detection and recognition, tamper detection, touch detection, attack detection, user authentication, driver fatigue detection, traffic monitoring, smoking detection, school violence detection, human counting, metal detection, human recognition, bike localization, human queue estimation, Wi-Fi imaging, and other types of wireless sensing applications. For instance, the wireless sensing system may operate as a motion detection system to detect the existence and location of motion based on Wi-Fi signals or other types of wireless signals.

The examples described herein may be useful for home monitoring. In some instances, home monitoring using the wireless sensing systems described herein may provide several advantages, including full home coverage through walls and in darkness, discreet detection without cameras, higher accuracy and reduced false alerts (e.g., in comparison with sensors that do not use Wi-Fi signals to sense their environments), and adjustable sensitivity. By layering Wi-Fi motion detection capabilities into routers and gateways, a robust motion detection system may be provided.

The examples described herein may also be useful for wellness monitoring. Caregivers want to know their loved ones are safe, while seniors and people with special needs want to maintain their independence at home with dignity. In some instances, wellness monitoring using the wireless sensing systems described herein may provide a solution that uses wireless signals to detect motion without using cameras or infringing on privacy, generates alerts when unusual activity is detected, tracks sleep patterns, and generates preventative health data. For example, caregivers can monitor motion, visits from health care professionals, and unusual behavior such as staying in bed longer than normal. Furthermore, motion is monitored unobtrusively without the need for wearable devices, and the wireless sensing systems described herein offer a more affordable and convenient alternative to assisted living facilities and other security and health monitoring tools.

The examples described herein may also be useful for setting up a smart home. In some examples, the wireless sensing systems described herein use predictive analytics and artificial intelligence (AI), to learn motion patterns and trigger smart home functions accordingly. Examples of smart home functions that may be triggered include adjusting the thermostat when a person walks through the front door, turning other smart devices on or off based on preferences, automatically adjusting lighting, adjusting HVAC systems based on present occupants, etc.

In some aspects of what is described here, wireless signals are communicated through a space over a time period by a wireless communication network including a plurality of wireless communication devices. The space includes a plurality of locations. Channel information is obtained based on the wireless signals. A motion detection system includes a motion detection engine and a pattern extraction engine. The motion detection engine of the motion detection system generates motion data based on the channel information. The motion data may include motion indicator values and motion localization values. The pattern extraction engine of the motion detection system generates activity data and one or more notifications based on the motion data and user input data. In some instances, the activity data can include an actual value of a metric of interest and a benchmark value of the metric of interest. The metric of interest can be or can be related to, for example, amount of sleep, amount of activity, amount of non-activity, amount of activity in a location, or a combination of these and other types of metrics. The activity data and the one or more notifications may be provided for display, for example, on a user interface of a user device. In some examples, the activity data and the one or more notifications are displayed to a user on a mobile device (e.g., on a smartphone or tablet) using a graphical user interface.

In some instances, aspects of the systems and techniques described here provide technical improvements and advantages over existing approaches. For example, higher-order information can be extracted from the motion data, and such higher-order information may inform the user of the user's activity and motion over various timeframes and locations. Additionally, the pattern extraction engine facilitates generation of motion-related user alerts responsive to determinations of activity level, location of motion, duration of motion, or the timing of motion occurrence. The technical improvements and advantages achieved in examples where the wireless sensing system is used for motion detection may also be achieved in other examples where the wireless sensing system is used for other wireless sensing applications.

In some instances, a wireless sensing system can be implemented using a wireless communication network. Wireless signals received at one or more wireless communication devices in the wireless communication network may be analyzed to determine channel information for the different communication links (between respective pairs of wireless communication devices) in the network. The channel information may be representative of a physical medium that applies a transfer function to wireless signals that traverse a space. In some instances, the channel information includes a channel response. Channel responses can characterize a physical communication path, representing the combined effect of, for example, scattering, fading, and power decay within the space between the transmitter and receiver. In some instances, the channel information includes beamforming state information (e.g., a feedback matrix, a steering matrix, channel state information (CSI), etc.) provided by a beamforming system. Beamforming is a signal processing technique often used in multi antenna (multiple-input/multiple-output (MIMO)) radio systems for directional signal transmission or reception. Beamforming can be achieved by operating elements in an antenna array in such a way that signals at particular angles experience constructive interference while others experience destructive interference.

The channel information for each of the communication links may be analyzed by one or more motion detection algorithms (e.g., running on a hub device, a client device, or other device in the wireless communication network, or on a remote device communicably coupled to the network) to detect, for example, whether motion has occurred in the space, to determine a relative location of the detected motion, or both. In some aspects, the channel information for each of the communication links may be analyzed to detect whether an object is present or absent, e.g., when no motion is detected in the space.

In some instances, a motion detection system returns motion data. In some implementations, the motion data indicate a degree of motion in the space, the location of motion in the space, a time at which the motion occurred, or a combination thereof. In some instances, wireless signals may be communicated through a space over a time period by a wireless communication network, and the motion data include motion indicator values indicative of a degree of motion that occurred in the space for each time point in a series of time points within the time period. In some implementations, the respective motion indicator values represent the degree of motion detected from the wireless signals exchanged on the respective wireless communication links in the network. In some instances, the space (e.g., a house) includes multiple locations (e.g., rooms or areas within the house), and the motion data include motion localization values for the individual locations, with the motion localization value for each individual location representing a relative degree of motion detected at the individual location for each time point in the series of time points within the time period. In some instances, the motion data include a motion score, which may include, or may be, one or more of the following: a scalar quantity indicative of a level of signal perturbation in the environment accessed by the wireless signals; an indication of whether there is motion; an indication of whether there is an object present; or an indication or classification of a gesture performed in the environment accessed by the wireless signals.

In some implementations, the motion detection system can be implemented using one or more motion detection algorithms. Example motion detection algorithms that can be used to detect motion based on wireless signals include the techniques described in U.S. Pat. No. 9,523,760 entitled "Detecting Motion Based on Repeated Wireless Transmissions," U.S. Pat. No. 9,584,974 entitled "Detecting Motion Based on Reference Signal Transmissions," U.S. Pat. No. 10,051,414 entitled "Detecting Motion Based On Decompositions Of Channel Response Variations," U.S. Pat. No. 10,048,350 entitled "Motion Detection Based on Groupings of Statistical Parameters of Wireless Signals," U.S. Pat. No. 10,108,903 entitled "Motion Detection Based on Machine Learning of Wireless Signal Properties," U.S. Pat. No. 10,109,167 entitled "Motion Localization in a Wireless Mesh Network Based on Motion Indicator Values," U.S. Pat. No. 10,109,168 entitled "Motion Localization Based on Channel Response Characteristics," U.S. Pat. No. 10,743,143 entitled "Determining a Motion Zone for a Location of Motion Detected by Wireless Signals," U.S. Pat. No. 10,605,908 entitled "Motion Detection Based on Beamforming Dynamic Information from Wireless Standard Client Devices," U.S. Pat. No. 10,605,907 entitled "Motion Detection by a Central Controller Using Beamforming Dynamic Information," U.S. Pat. No. 10,600,314 entitled "Modifying Sensitivity Settings in a Motion Detection System," U.S. Pat. No. 10,567,914 entitled "Initializing Probability Vectors for Determining a Location of Motion Detected from Wireless Signals," U.S. Pat. No. 10,565,860 entitled "Offline Tuning System for Detecting New Motion Zones in a Motion Detection System," U.S. Pat. No. 10,506,384 entitled "Determining a Location of Motion Detected from Wireless Signals Based on Prior Probability," U.S. Pat. No. 10,499,364 entitled "Identifying Static Leaf Nodes in a Motion Detection System," U.S. Pat. No. 10,498,467 entitled "Classifying Static Leaf Nodes in a Motion Detection System," U.S. Pat. No. 10,460,581 entitled "Determining a Confidence for a Motion Zone Identified as a Location of Motion for Motion Detected by Wireless Signals," U.S. Pat. No. 10,459,076 entitled "Motion Detection based on Beamforming Dynamic Information," U.S. Pat. No. 10,459,074 entitled "Determining a Location of Motion Detected from Wireless Signals Based on Wireless Link Counting," U.S. Pat. No. 10,438,468 entitled "Motion Localization in a Wireless Mesh Network Based on Motion Indicator Values," U.S. Pat. No. 10,404,387 entitled "Determining Motion Zones in a Space Traversed by Wireless Signals," U.S. Pat. No. 10,393,866 entitled "Detecting Presence Based on Wireless Signal Analysis," U.S. Pat. No. 10,380,856 entitled "Motion Localization Based on Channel Response Characteristics," U.S. Pat. No. 10,318,890 entitled "Training Data for a Motion Detection System using Data from a Sensor Device," U.S. Pat. No. 10,264,405 entitled "Motion Detection in Mesh Networks," U.S. Pat. No. 10,228,439 entitled "Motion Detection Based on Filtered Statistical Parameters of Wireless Signals," U.S. Pat. No. 10,129,853 entitled "Operating a Motion Detection Channel in a Wireless Communication Network," U.S. Pat. No. 10,111,228 entitled "Selecting Wireless Communication Channels Based on Signal Quality Metrics," and other techniques.

FIG. 1 illustrates an example wireless communication system 100. The wireless communication system 100 may perform one or more operations of a motion detection system. The technical improvements and advantages achieved from using the wireless communication system 100 to detect motion are also applicable in examples where the wireless communication system 100 is used for another wireless sensing application.

The example wireless communication system 100 includes three wireless communication devices 102A, 102B, 102C. The example wireless communication system 100 may include additional wireless communication devices 102 and/or other components (e.g., one or more network servers, network routers, network switches, cables, or other communication links, etc.).

The example wireless communication devices 102A, 102B, 102C can operate in a wireless network, for example, according to a wireless network standard or another type of wireless communication protocol. For example, the wireless network may be configured to operate as a Wireless Local Area Network (WLAN), a Personal Area Network (PAN), a Metropolitan Area Network (MAN), or another type of wireless network. Examples of WLANs include networks configured to operate according to one or more of the 802.11 family of standards developed by IEEE (e.g., Wi-Fi networks), and others. Examples of PANs include networks that operate according to short-range communication standards (e.g., BLUETOOTH®, Near Field Communication (NFC), ZigBee), millimeter wave communications, and others.

In some implementations, the wireless communication devices 102A. 102B, 102C may be configured to communicate in a cellular network, for example, according to a cellular network standard. Examples of cellular networks include: networks configured according to 2G standards such as Global System for Mobile (GSM) and Enhanced Data rates for GSM Evolution (EDGE) or EGPRS; 3G standards such as Code Division Multiple Access (CDMA), Wideband Code Division Multiple Access (WCDMA), Universal Mobile Telecommunications System (UMTS), and Time Division Synchronous Code Division Multiple Access (TD-SCDMA); 4G standards such as Long-Term Evolution (LTE) and LTE-Advanced (LTE-A); 5G standards, and others.

In some cases, one or more of the wireless communication devices 102 can be a Wi-Fi access point or another type of wireless access point (WAP). In some cases, one or more of the wireless communication devices 102 is an access point of a wireless mesh network, such as, for example, a commercially-available mesh network system (e.g., GOOGLE Wi-Fi, EERO mesh, etc.). In some instances, one or more of the wireless communication devices 102 can be implemented as wireless access points (APs) in a mesh network, while the other wireless communication device(s) 102 are implemented as leaf devices (e.g., mobile devices, smart devices, etc.) that access the mesh network through one of the APs. In some cases, one or more of the wireless communication devices 102 is a mobile device (e.g., a smartphone, a smart watch, a tablet, a laptop computer, etc.), a wireless-enabled device (e.g., a smart thermostat, a Wi-Fi enabled camera, a smart TV), or another type of device that communicates in a wireless network.

In the example shown in FIG. 1, the wireless communication devices transmit wireless signals to each other over wireless communication links (e.g., according to a wireless network standard or a non-standard wireless communication protocol), and the wireless signals communicated between the devices can be used as motion probes to detect motion of objects in the signal paths between the devices. In some implementations, standard signals (e.g., channel sounding signals, beacon signals), non-standard reference signals, or other types of wireless signals can be used as motion probes.

In the example shown in FIG. 1, the wireless communication link between the wireless communication devices 102A. 102C can be used to probe a first motion detection zone 110A, the wireless communication link between the wireless communication devices 102B, 102C can be used to probe a second motion detection zone 110B, and the wireless communication link between the wireless communication devices 102A, 102B can be used to probe a third motion detection zone 110C. In some instances, the motion detection zones 110 can include, for example, air, solid materials, liquids, or another medium through which wireless electromagnetic signals may propagate.

In the example shown in FIG. 1, when an object moves in any of the motion detection zones 110, the motion detection system may detect the motion based on signals transmitted through the relevant motion detection zone 110. Generally, the object can be any type of static or moveable object, and can be living or inanimate. For example, the object can be a human (e.g., the person 106 shown in FIG. 1), an animal, an inorganic object, or another device, apparatus, or assembly, an object that defines all or part of the boundary of a space (e.g., a wall, door, window, etc.), or another type of object.

In some examples, the wireless signals propagate through a structure (e.g., a wall) before or after interacting with a moving object, which may allow the object's motion to be detected without an optical line-of-sight between the moving object and the transmission or receiving hardware. In some instances, the motion detection system may communicate the motion detection event to another device or system, such as a security system or a control center.

In some cases, the wireless communication devices 102 themselves are configured to perform one or more operations of the motion detection system, for example, by executing computer-readable instructions (e.g., software or firmware) on the wireless communication devices. For example, each device may process received wireless signals to detect motion based on changes in the communication channel. In some cases, another device (e.g., a remote server, a cloud-based computer system, a network-attached device, etc.) is configured to perform one or more operations of the motion detection system. For example, each wireless communication device 102 may send channel information to a specified device, system, or service that performs operations of the motion detection system.

In an example aspect of operation, wireless communication devices 102A, 102B may broadcast wireless signals or address wireless signals to the other wireless communication device 102C, and the wireless communication device 102C (and potentially other devices) receives the wireless signals transmitted by the wireless communication devices 102A, 102B. The wireless communication device 102C (or another system or device) then processes the received wireless signals to detect motion of an object in a space accessed by the wireless signals (e.g., in the zones 110A, 11B). In some instances, the wireless communication device 102C (or another system or device) may perform one or more operations of a motion detection system.

Figure 2A:
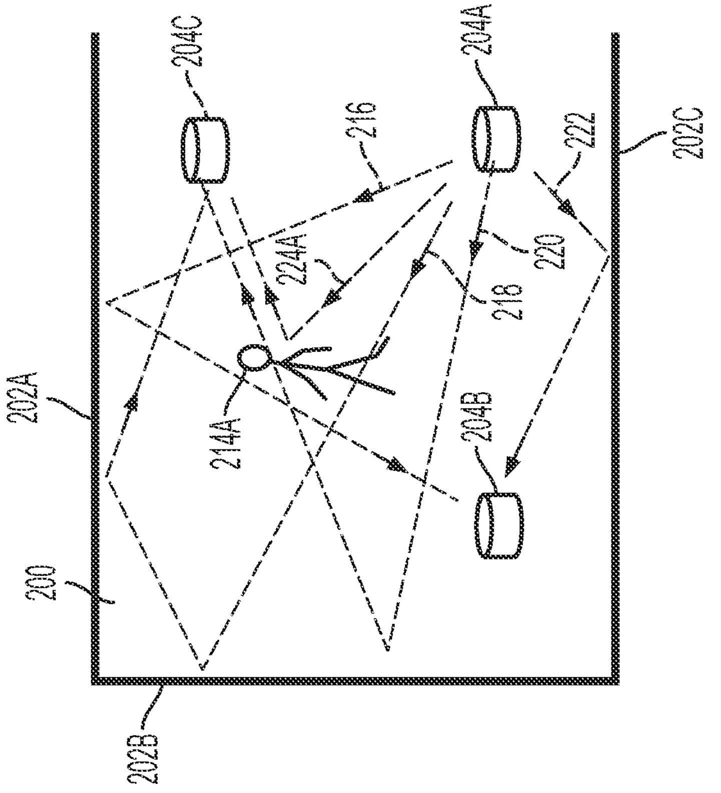
FIGS. 2A-2B are diagrams showing example wireless signals communicated between wireless communication devices.
Figure 2B:
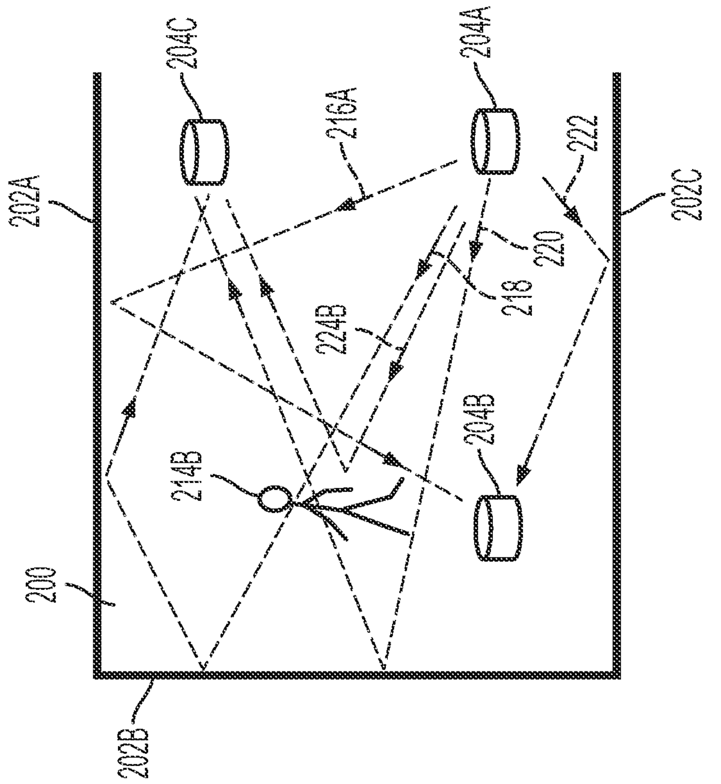

FIGS. 2A and 2B are diagrams showing example wireless signals communicated between wireless communication devices 204A, 204B, 204C. The wireless communication devices 204A, 204B, 204C can be, for example, the wireless communication devices 102A, 102B, 102C shown in FIG. 1, or may be other types of wireless communication devices.

In some cases, a combination of one or more of the wireless communication devices 204A, 204B, 204C can be part of, or may be used by, a motion detection system. The example wireless communication devices 204A, 204B, 204C can transmit wireless signals through a space 200. The example space 200 may be completely or partially enclosed or open at one or more boundaries of the space 200. The space 200 may be or may include an interior of a room, multiple rooms, a building, an indoor area, outdoor area, or the like. A first wall 202A, a second wall 202B, and a third wall 202C at least partially enclose the space 200 in the example shown.

In the example shown in FIGS. 2A and 2B, the first wireless communication device 204A transmits wireless motion probe signals repeatedly (e.g., periodically, intermittently, at scheduled, unscheduled, or random intervals, etc.). The second and third wireless communication devices 204B, 204C receive signals based on the motion probe signals transmitted by the wireless communication device 204A.

As shown, an object is in a first position 214A at an initial time (t0) in FIG. 2A, and the object has moved to a second position 214B at subsequent time (t1) in FIG. 2B. In FIGS. 2A and 2B, the moving object in the space 200 is represented as a human, but the moving object can be another type of object. For example, the moving object can be an animal, an inorganic object (e.g., a system, device, apparatus, or assembly), an object that defines all or part of the boundary of the space 200 (e.g., a wall, door, window, etc.), or another type of object. In the example shown in FIGS. 2A and 2B, the wireless communication devices 204A, 204B, 204C are stationary and are, consequently, at the same position at the initial time t0 and at the subsequent time t1. However, in other examples, one or more of the wireless communication devices 204A, 204B, 204C are mobile and may move between initial time t0 and subsequent time t1.

As shown in FIGS. 2A and 2B, multiple example paths of the wireless signals transmitted from the first wireless communication device 204A are illustrated by dashed lines. Along a first signal path 216, the wireless signal is transmitted from the first wireless communication device 204A and reflected off the first wall 202A toward the second wireless communication device 204B. Along a second signal path 218, the wireless signal is transmitted from the first wireless communication device 204A and reflected off the second wall 202B and the first wall 202A toward the third wireless communication device 204C. Along a third signal path 220, the wireless signal is transmitted from the first wireless communication device 204A and reflected off the second wall 202B toward the third wireless communication device 204C. Along a fourth signal path 222, the wireless signal is transmitted from the first wireless communication device 204A and reflected off the third wall 202C toward the second wireless communication device 204B.

In FIG. 2A, along a fifth signal path 224A, the wireless signal is transmitted from the first wireless communication device 204A and reflected off the object at the first position 214A toward the third wireless communication device 204C. Between time t0 in FIG. 2A and time t1 in FIG. 2B, the object moves from the first position 214A to a second position 214B in the space 200 (e.g., some distance away from the first position 214A). In FIG. 2B, along a sixth signal path 224B, the wireless signal is transmitted from the first wireless communication device 204A and reflected off the object at the second position 214B toward the third wireless communication device 204C. The sixth signal path 224B depicted in FIG. 2B is longer than the fifth signal path 224A depicted in FIG. 2A due to the movement of the object from the first position 214A to the second position 214B. In some examples, a signal path can be added, removed, or otherwise modified due to movement of an object in a space.

The example wireless signals shown in FIGS. 2A and 2B can experience attenuation, frequency shifts, phase shifts, or other effects through their respective paths and may have portions that propagate in another direction, for example, through the walls 202A, 202B, and 202C. In some examples, the wireless signals are radio frequency (RF) signals. The wireless signals may include other types of signals.

The transmitted signal can have a number of frequency components in a frequency bandwidth, and the transmitted signal may include one or more bands within the frequency bandwidth. The transmitted signal may be transmitted from the first wireless communication device 204A in an omnidirectional manner, in a directional manner, or otherwise. In the example shown, the wireless signals traverse multiple respective paths in the space 200, and the signal along each path can become attenuated due to path losses, scattering, reflection, or the like and may have a phase or frequency offset.

As shown in FIGS. 2A and 2B, the signals from various paths 216, 218, 220, 222, 224A, and 224B combine at the third wireless communication device 204C and the second wireless communication device 204B to form received signals. Because of the effects of the multiple paths in the space 200 on the transmitted signal, the space 200 may be represented as a transfer function (e.g., a filter) in which the transmitted signal is input and the received signal is output. When an object moves in the space 200, the attenuation or phase offset applied to a wireless signal along a signal path can change, and hence, the transfer function of the space 200 can change. When the same wireless signal is transmitted from the first wireless communication device 204A, if the transfer function of the space 200 changes, the output of that transfer function, e.g. the received signal, can also change. A change in the received signal can be used to detect motion of an object. Conversely, in some cases, if the transfer function of the space does not change, the output of the transfer function—the received signal—may not change.

Figure 2C:
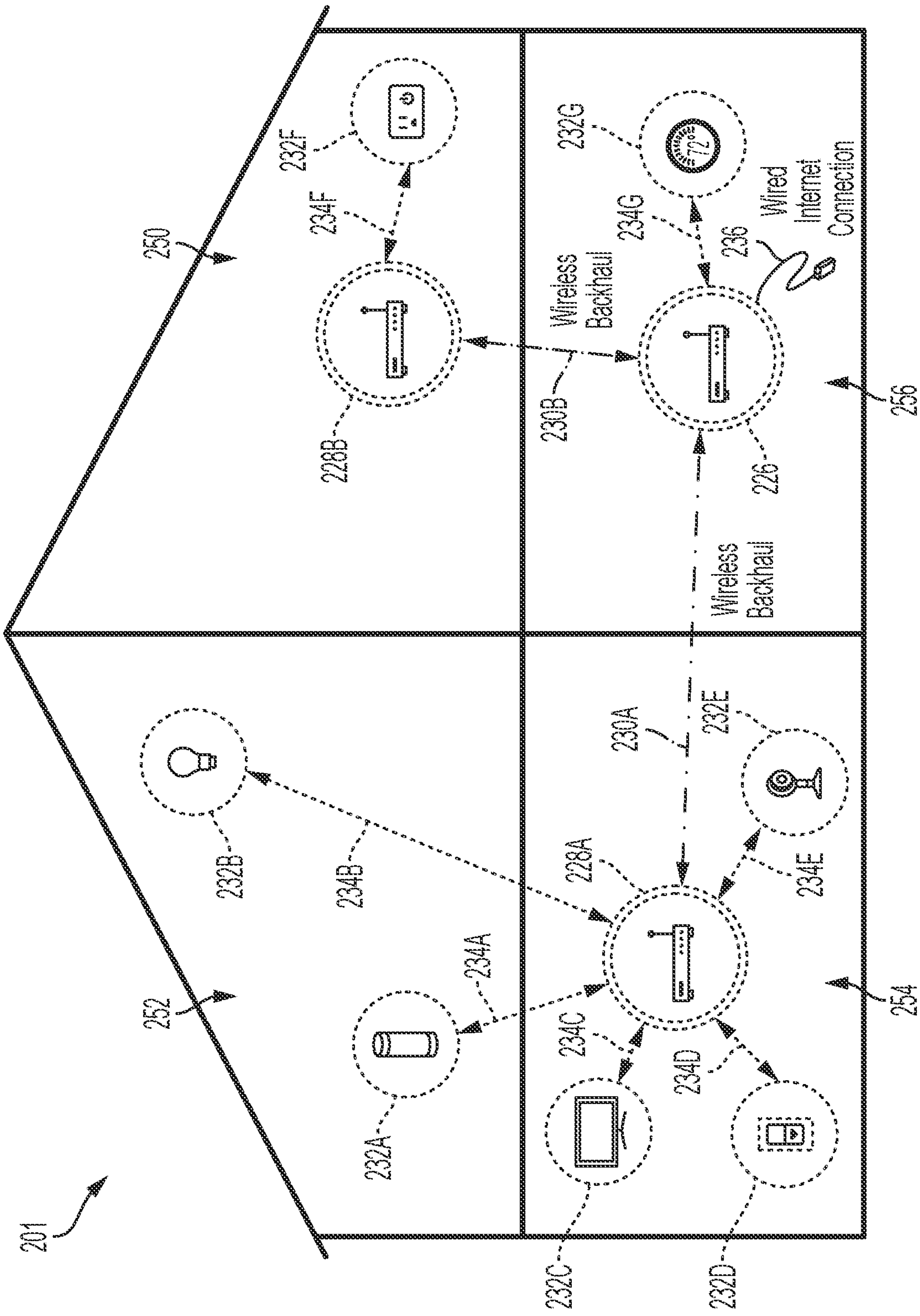
FIG. 2C is a diagram showing an example wireless sensing system operating to detect motion in a space.

FIG. 2C is a diagram showing an example wireless sensing system operating to detect motion in a space 201. The example space 201 shown in FIG. 2C is a home that includes multiple locations (e.g., distinct spatial regions or zones). In the example shown, the space 201 includes a first location 250 (e.g., a first bedroom), a second location 252 (e.g., a second bedroom), a third location 254 (e.g., a living room), and a fourth location 256 (e.g., a kitchen area). In the example shown, the wireless motion detection system uses a multi-AP home network topology (e.g., mesh network or a Self-Organizing-Network (SON)), which includes three access points (APs): a central access point 226 and two extension access points 228A, 228B. In a typical multi-AP home network, each AP typically supports multiple bands (2.4G, 5G, 6G), and multiple bands may be enabled at the same time. Each AP can use a different Wi-Fi channel to serve its clients, as this may allow for better spectrum efficiency.

In the example shown in FIG. 2C, the wireless communication network includes a central access point 226. In a multi-AP home Wi-Fi network, one AP may be denoted as the central AP. This selection, which is often managed by manufacturer software running on each AP, is typically the AP that has a wired Internet connection 236. The other APs 228A, 228B connect to the central AP 226 wirelessly, through respective wireless backhaul connections 230A, 230B. The central AP 226 may select a wireless channel different from the extension APs to serve its connected clients.

In the example shown in FIG. 2C, the extension APs 228A, 228B extend the range of the central AP 226, by allowing devices to connect to a potentially closer AP or different channel. The end user need not be aware of which AP the device has connected to, as all services and connectivity would generally be identical. In addition to serving all connected clients, the extension APs 228A, 228B connect to the central AP 226 using the wireless backhaul connections 230A, 230B to move network traffic between other APs and provide a gateway to the Internet. Each extension AP 228A, 228B may select a different channel to serve its connected clients.

In the example shown in FIG. 2C, client devices (e.g., Wi-Fi client devices) 232A, 232B, 232C, 232D, 232E, 232F, 232G are associated with either the central AP 226 or one of the extension APs 228 using a respective wireless link 234A, 234B, 234C, 234D, 234E, 234F, 234G. The client devices 232 that connect to the multi-AP network may operate as leaf nodes in the multi-AP network. In some implementations, the client devices 232 may include wireless-enabled devices (e.g., mobile devices, a smartphone, a smart watch, a tablet, a laptop computer, a smart thermostat, a wireless-enabled camera, a smart TV, a wireless-enabled speaker, a wireless-enabled power socket, etc.).

When the client devices 232 seek to connect to and associate with their respective APs 226, 228, the client devices 232 may go through an authentication and association phase with their respective APs 226, 228. Among other things, the association phase assigns address information (e.g., an association ID or another type of unique identifier) to each of the client devices 232. For example, within the IEEE 802.11 family of standards for Wi-Fi, each of the client devices 232 can identify itself using a unique address (e.g., a 48-bit address, an example being the MAC address), although the client devices 232 may be identified using other types of identifiers embedded within one or more fields of a message. The address information (e.g., MAC address or another type of unique identifier) can be either hardcoded and fixed, or randomly generated according to the network address rules at the start of the association process. Once the client devices 232 have associated to their respective APs 226, 228, their respective address information may remain fixed. Subsequently, a transmission by the APs 226, 228 or the client devices 232 typically includes the address information (e.g., MAC address) of the transmitting wireless device and the address information (e.g., MAC address) of the receiving device.

In the example shown in FIG. 2C, the wireless backhaul connections 230A, 230B carry data between the APs and may also be used for motion detection. Each of the wireless backhaul channels (or frequency bands) may be different than the channels (or frequency bands) used for serving the connected Wi-Fi devices.

In the example shown in FIG. 2C, wireless links 234A, 234B, 234C, 234D, 234E, 234F, 234G may include a frequency channel used by the client devices 232A, 232B, 232C, 232D, 232E, 232F, 232G to communicate with their respective APs 226, 228. Each AP can select its own channel independently to serve their respective client devices, and the wireless links 234 may be used for data communications as well as motion detection.

The motion detection system, which may include one or more motion detection or localization processes running on one or more of the client devices 232 or on one or more of the APs 226, 228, may collect and process data (e.g., channel information) corresponding to local links that are participating in the operation of the wireless sensing system. The motion detection system can be installed as a software or firmware application on the client devices 232 or on the APs 226, 228, or may be part of the operating systems of the client devices 232 or the APs 226, 228.

In some implementations, the APs 226, 228 do not contain motion detection software and are not otherwise configured to perform motion detection in the space 201. Instead, in such implementations, the operations of the motion detection system are executed on one or more of the client devices 232. In some implementations, the channel information may be obtained by the client devices 232 by receiving wireless signals from the APs 226, 228 (or possibly from other client devices 232) and processing the wireless signal to obtain the channel information. For example, the motion detection system running on the client devices 232 can have access to channel information provided by the client device's radio firmware (e.g., Wi-Fi radio firmware) so that channel information may be collected and processed.

In some implementations, the client devices 232 send a request to their corresponding AP 226, 228 to transmit wireless signals that can be used by the client device as motion probes to detect motion of objects in the space 201. The request sent to the corresponding AP 226, 228 may be a null data packet frame, a beamforming request, a ping, standard data traffic, or a combination thereof. In some implementations, the client devices 232 are stationary while performing motion detection in the space 201. In other examples, one or more of the client devices 232 can be mobile and may move within the space 201 while performing motion detection.

Mathematically, a signal f(t) transmitted from a wireless communication device (e.g., the wireless communication device 204A in FIGS. 2A and 2B or the APs 226, 228 in FIG. 2C) may be described according to Equation (1):

$$f(t)=\sum_{n=-\infty}^{\infty} c_n e^{j\omega_n t} \tag{1}$$

where $\omega_n$ represents the frequency of $n^{th}$ frequency component of the transmitted signal, $c_n$ represents the complex coefficient of the $n^{th}$ frequency component, and t represents time. With the transmitted signal f(t) being transmitted, an output signal $r_k(t)$ from a path k may be described according to Equation (2):

$$r_k(t)=\sum_{n=-\infty}^{\infty} \alpha_{n,k} c_n e^{j(\omega_n t+\phi_{n,k})} \tag{2}$$

where $\alpha_{n,k}$ represents an attenuation factor (or channel response; e.g., due to scattering, reflection, and path losses) for the $n^{th}$ frequency component along path k, and $\phi_{n,k}$ represents the phase of the signal for $n^{th}$ frequency component along path k. Then, the received signal R at a wireless communication device can be described as the summation of all output signals $r_k(t)$ from all paths to the wireless communication device, which is shown in Equation (3):

$$R=\sum_k r_k(t) \tag{3}$$

Substituting Equation (2) into Equation (3) renders the following Equation (4):

$$R=\sum_k \sum_{n=-\infty}^{\infty} (\alpha_{n,k} e^{j\phi_{n,k}}) c_n e^{j\omega_n t} \tag{4}$$

The received signal R at a wireless communication device (e.g., the wireless communication devices 204B, 204C in FIGS. 2A and 2B or the client devices 232 in FIG. 2C) can then be analyzed (e.g., using one or more motion detection algorithms) to detect motion. The received signal R at a wireless communication device can be transformed to the frequency domain, for example, using a Fast Fourier Transform (FFT) or another type of algorithm. The transformed signal can represent the received signal R as a series of n complex values, one for each of the respective frequency components (at the n frequencies $\omega_{Wn}$). For a frequency component at frequency $\omega_n$, a complex value $Y_n$ may be represented as follows in Equation (5):

$$Y_n=\sum_k c_n \alpha_{n,k} e^{j\phi_{n,k}}. \tag{5}$$

The complex value $Y_n$ for a given frequency component $\omega_n$ indicates a relative magnitude and phase offset of the received signal at that frequency component $\omega_n$. The signal f(t) may be repeatedly transmitted within a time period, and the complex value $Y_n$ can be obtained for each transmitted signal f(t). When an object moves in the space, the complex value $Y_n$ changes over the time period due to the channel response $\alpha_{n,k}$ of the space changing. Accordingly, a change detected in the channel response (and thus, the complex value $Y_n$) can be indicative of motion of an object within the communication channel. Conversely, a stable channel response may indicate lack of motion. Thus, in some implementations, the complex values $Y_n$ for each of multiple devices in a wireless network can be processed to detect whether motion has occurred in a space traversed by the transmitted signals f(t). The channel response can be expressed in either the time-domain or frequency-domain, and the Fourier-Transform or Inverse-Fourier-Transform can be used to switch between the time-domain expression of the channel response and the frequency-domain expression of the channel response.

In another aspect of FIGS. 2A, 2B, 2C, beamforming state information may be used to detect whether motion has occurred in a space traversed by the transmitted signals f(t). For example, beamforming may be performed between devices based on some knowledge of the communication channel (e.g., through feedback properties generated by a receiver), which can be used to generate one or more steering properties (e.g., a steering matrix) that are applied by a transmitter device to shape the transmitted beam/signal in a particular direction or directions. In some instances, changes to the steering or feedback properties used in the beamforming process indicate changes, which may be caused by moving objects in the space accessed by the wireless signals. For example, motion may be detected by identifying substantial changes in the communication channel, e.g. as indicated by a channel response, or steering or feedback properties, or any combination thereof, over a period of time.

In some implementations, for example, a steering matrix may be generated at a transmitter device (beamformer) based on a feedback matrix provided by a receiver device (beamformee) based on channel sounding. Because the steering and feedback matrices are related to propagation characteristics of the channel, these beamforming matrices change as objects move within the channel. Changes in the channel characteristics are accordingly reflected in these matrices, and by analyzing the matrices, motion can be detected, and different characteristics of the detected motion can be determined. In some implementations, a spatial map may be generated based on one or more beamforming matrices. The spatial map may indicate a general direction of an object in a space relative to a wireless communication device. In some cases, "modes" of a beamforming matrix (e.g., a feedback matrix or steering matrix) can be used to generate the spatial map. The spatial map may be used to detect the presence of motion in the space or to detect a location of the detected motion.

Figure 3:
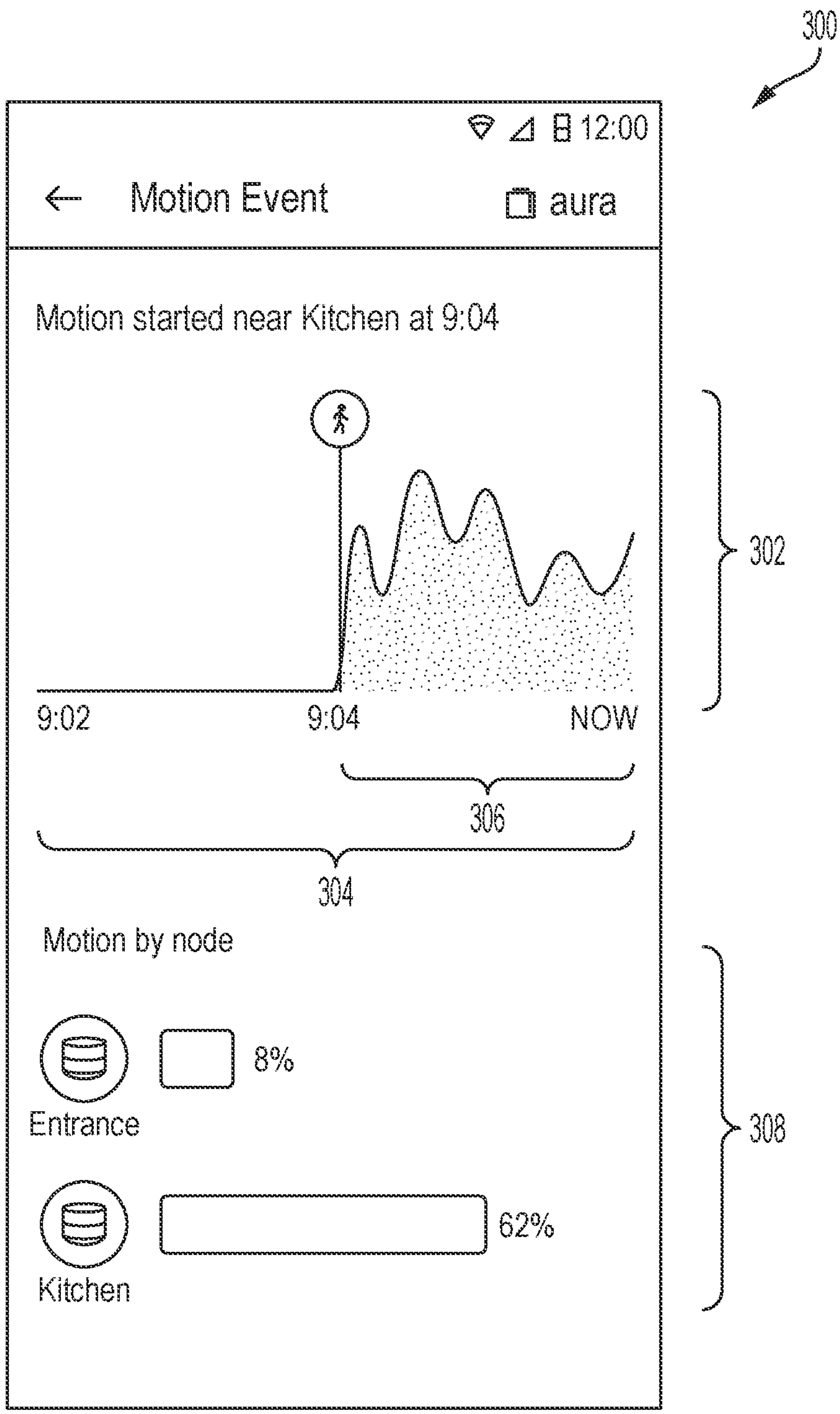
FIG. 3 is a diagram showing an example graphical display on a user interface of a user device.

In some implementations, the output of the motion detection system may be provided as a notification for graphical display on a user interface of a user device. FIG. 3 is a diagram showing an example graphical display on a user interface 300 on a user device. In some implementations, the user device is the client device 232 used to detect motion, a user device of a caregiver or emergency contact designated to an individual in the space 200, 201, or any other user device that is communicatively coupled to the motion detection system to receive notifications from the motion detection system. As an example, the user interface 300 may be a graphic display shown on a dashboard for third party services (e.g., professional monitoring centers or caregiver organizations that monitor the safety of a person, such as the elderly).

The example user interface 300 shown in FIG. 3 includes an element 302 that displays motion data generated by the motion detection system. As shown in FIG. 3, the element 302 includes a horizontal timeline that includes a time period 304 (including a series of time points 306) and a plot of motion data indicating a degree of motion detected by the motion detection system for each time point in the series of time points 306. In the example shown, the user is notified that the detected motion started near a particular location (e.g., the kitchen) at a particular time (e.g., 9:04), and the relative degree of motion detected is indicated by the height of the curve at each time point.

The example user interface 300 shown in FIG. 3 also includes an element 308 that displays the relative degree of motion detected by each node of the motion detection system. In particular, the element 308 indicates that 8% of the motion was detected by the "Entrance" node (e.g., an AP installed at the home entry) while 62% of the motion was detected by the "Kitchen" node (e.g., an AP installed in the kitchen). The data provided in the elements 302, 308 can help the user determine an appropriate action to take in response to the motion detection event, correlate the motion detection event with the user's observation or knowledge, determine whether the motion detection event was true or false, etc. The user interface 300 shown in FIG. 3 may include other (e.g., additional or alternative) elements. For example, in some instances, the user interface may include an element that displays a sequence of locations where motion was detected over a series of sequential time points. As an illustration, referring to the space 201 shown in FIG. 2C, the user interface can indicate that motion was first detected at location 250 at a first time point, followed by location 252 at a second, later time point, location 254 at a third, later time point, and location 256 at a fourth, later time point. In such instances, a user may infer, from the information displayed on the user interface, that an object was moving along a path that commenced at location 250 and proceeded to locations 252, 254, and 256, in that order. In some instances, a user can select (e.g., by the user's finger touch on the client device's touch screen) one or more locations displayed on the user interface to obtain information related to motion in the selected location (e.g., an indication of a time when motion started or was detected in the selected location).

In some implementations, the output of the motion detection system is provided in real-time (e.g., to an end user). Additionally or alternatively, the output of the motion detection system can be stored (e.g., locally on the wireless communication devices 204, client devices 232, the APs 226, 228, or on a cloud-based storage service) and analyzed to reveal statistical information over a time frame (e.g., hours, days, or months). An example where the output of the motion detection system may be stored and analyzed to reveal statistical information over a time frame is in health monitoring, vital sign monitoring, sleep monitoring, etc. In some implementations, an alert (e.g., a notification, an audio alert, or a video alert) is provided based on the output of the motion detection system. For example, a motion detection event may be communicated to another device or system (e.g., a security system or a control center), a designated caregiver, a professional monitoring center that receives the alert and reacts to it, or a designated emergency contact based on the output of the motion detection system.

Figure 4:
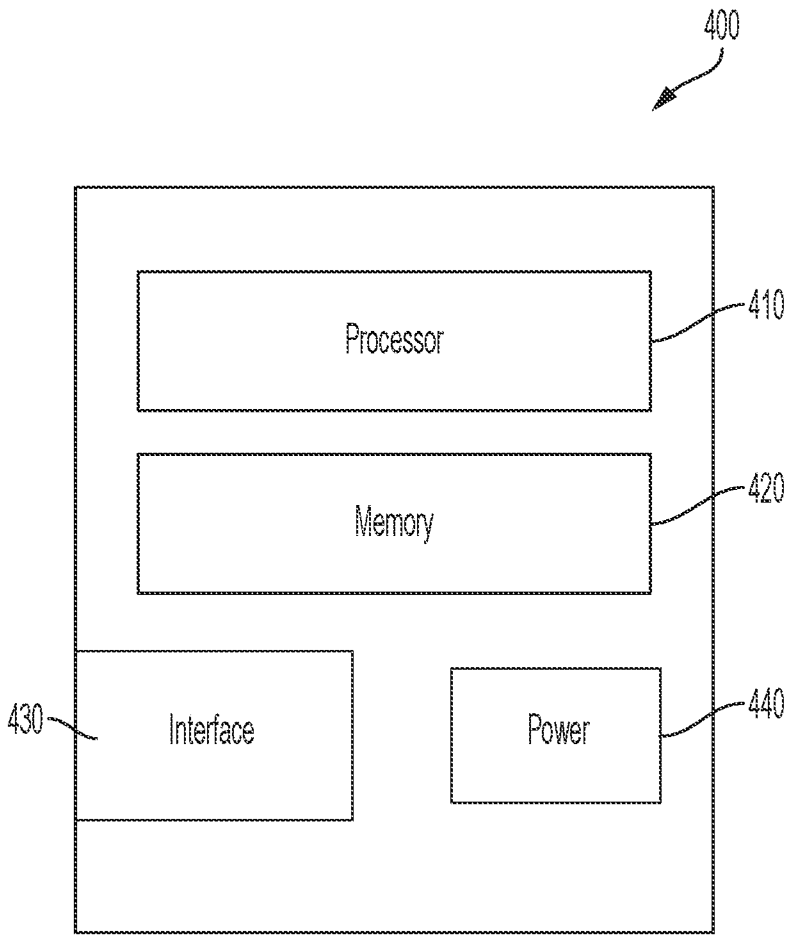
FIG. 4 is a block diagram showing an example wireless communication device.

FIG. 4 is a block diagram showing an example wireless communication device 400. As shown in FIG. 4, the example wireless communication device 400 includes an interface 430, a processor 410, a memory 420, and a power unit 440. A wireless communication device (e.g., any of the wireless communication devices 102A, 102B, 102C in FIG. 1, wireless communication devices 204A, 204B, 204C in FIGS. 2A and 2B, the client devices 232 and APs 226, 228 in FIG. 2C) may include additional or different components, and the wireless communication device 400 may be configured to operate as described with respect to the examples above. In some implementations, the interface 430, processor 410, memory 420, and power unit 440 of a wireless communication device are housed together in a common housing or other assembly. In some implementations, one or more of the components of a wireless communication device can be housed separately, for example, in a separate housing or other assembly.

The example interface 430 can communicate (receive, transmit, or both) wireless signals. For example, the interface 430 may be configured to communicate radio frequency (RF) signals formatted according to a wireless communication standard (e.g., Wi-Fi, 4G, 5G, Bluetooth, etc.). In some implementations, the example interface 430 includes a radio subsystem and a baseband subsystem. The radio subsystem may include, for example, one or more antennas and radio frequency circuitry. The radio subsystem can be configured to communicate radio frequency wireless signals on the wireless communication channels. As an example, the radio subsystem may include a radio chip, an RF front end, and one or more antennas. The baseband subsystem may include, for example, digital electronics configured to process digital baseband data. In some cases, the baseband subsystem includes a digital signal processor (DSP) device or another type of processor device. In some cases, the baseband system includes digital processing logic to operate the radio subsystem, to communicate wireless network traffic through the radio subsystem or to perform other types of processes.

The example processor 410 can execute instructions, for example, to generate output data based on data inputs. The instructions can include programs, codes, scripts, modules, or other types of data stored in memory 420. Additionally or alternatively, the instructions can be encoded as pre-programmed or re-programmable logic circuits, logic gates, or other types of hardware or firmware components or modules. The processor 410 may be or include a general-purpose microprocessor, as a specialized co-processor or another type of data processing apparatus. In some cases, the processor 410 performs high level operation of the wireless communication device 400. For example, the processor 410 may be configured to execute or interpret software, scripts, programs, functions, executables, or other instructions stored in the memory 420. In some implementations, the processor 410 is included in the interface 430 or another component of the wireless communication device 400.

The example memory 420 may include computer-readable storage media, for example, a volatile memory device, a non-volatile memory device, or both. The memory 420 may include one or more read-only memory devices, random-access memory devices, buffer memory devices, or a combination of these and other types of memory devices. In some instances, one or more components of the memory can be integrated or otherwise associated with another component of the wireless communication device 400. The memory 420 may store instructions that are executable by the processor 410. For example, the instructions may include instructions to perform one or more of the operations in the example process 1000 shown in FIG. 10 or the example process 1100 shown in FIG. 11.

The example power unit 440 provides power to the other components of the wireless communication device 400. For example, the other components may operate based on electrical power provided by the power unit 440 through a voltage bus or other connection. In some implementations, the power unit 440 includes a battery or a battery system, for example, a rechargeable battery. In some implementations, the power unit 440 includes an adapter (e.g., an AC adapter) that receives an external power signal (from an external source) and converts the external power signal to an internal power signal conditioned for a component of the wireless communication device 400. The power unit 420 may include other components or operate in another manner.

Figure 5:
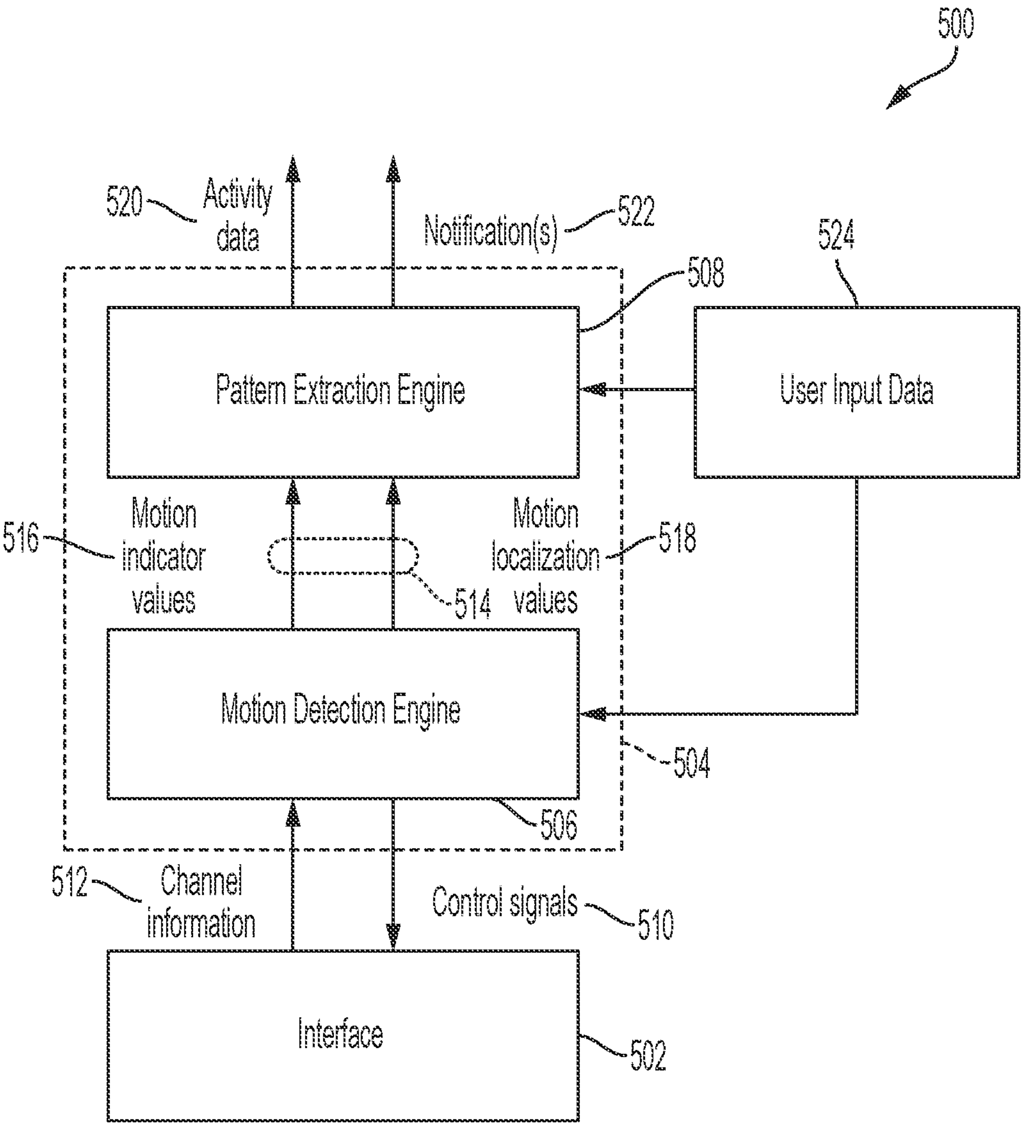
FIG. 5 is a block diagram showing an example system for generating activity data and at least one notification for display on a user interface of a wireless communication device.

FIG. 5 is a block diagram showing an example system 500 for generating activity data and at least one notification for display on a user interface of a wireless communication device. In some implementations, the wireless communication device may be a user device. In some implementations, the user device is the client device 232 shown in FIG. 2C, a user device of a caregiver or emergency contact designated to an individual in the space 200, 201, or any other user device that is communicatively coupled to the system 500.

The example system 500 includes an interface 502 configured to communicate wireless signals (e.g., radio frequency (RF) signals), formatted according to a wireless communication standard (e.g., Wi-Fi, 4G, 5G, Bluetooth, etc.), through a space (e.g., the space 200 or 201). In some implementations, the interface 502 can be identified with the interface 430 shown in FIG. 4. The example system 500 includes a motion detection system 504, which includes a motion detection engine 506 and a pattern extraction engine 508. In some implementations, the motion detection system 504 controls the operation of the interface 502 (e.g., via control signals 510). In some instances, the control signals 510 determine the series of time points (e.g., time points 306 shown in FIG. 3) within a time period (e.g., the time period 304 shown in FIG. 3) during which the wireless signals are communicated through the space. The interface 502 may generate channel information 512 based on the wireless signals that are communicated through the space.

The motion detection system 504 receives the channel information 512 from the interface 502. In some implementations, operation of the motion detection engine 506 may depend, at least in part, on input data provided by a user (e.g., shown in in FIG. 5 as user input data 524). The user input data 524 can be provided by the user through the user's interaction with an application running the motion detection system 500. In some instances, the user input data 524 can be obtained from geofencing data provided by the user (e.g., information related to the space in which motion is being detected), from the user's indication of an operating state of the motion detection system 500, or from any other source. In a first operating state (e.g., an Away mode), the motion detection system 500 may detect motion in space based on an assumption that no persons are present in the space or any of its locations. In a second operating state (e.g., a Home mode), the motion detection system 500 may detect motion in space based on an assumption that at least one person is present in the space or in its locations. In some instances, a user can enable or disable (e.g., through user input data 524) channel sounding (and thus motion detection) in one or more wireless communication devices (e.g., devices 226, 228, 232 shown in FIG. 2C) spatially distributed in a space in which motion is being detected. In some instances, a user can adjust (e.g., through user input data 524) the sensitivity of one or more wireless communication devices (e.g., the devices 226, 228, 232 shown in FIG. 2C) to motion, thereby adjusting the sensitivity of the motion detection system 500 to motion. In some implementations, the motion detection engine 506 generates motion data 514 based on the channel information 512 (e.g., using one or more motion detection algorithms discussed above). The motion data 514 may include motion indicator values 516, $m_t$, indicative of a degree of motion that occurred in the space for each time point t in the series of time points within the time period. Each of the motion indicator values $m_t$ can, as an example, be a value indicative of the aggregate degree of motion that occurred in the entire space at the time point t. For example, a motion indicator value $m_0$ can be a value indicative of the aggregate degree of motion that occurred in the entire 201 at time point to, while a motion indicator value $m_1$ can be a value indicative of the aggregate degree of motion that occurred in the entire 201 at time point $t_1$.

The motion data 514 may also include a motion localization vector $\hat{L}_t$ 518 for each time point t in the series of time points within the time period. The motion localization vector $\hat{L}_t$ 518 for the time point t may include entries of motion localization values $[L_{t,1}\ L_{t,2} \ldots L_{t,N}]$, where N is the number of locations in the space. In some instances, the motion localization vector $\hat{L}_t$ indicates the relative degree of motion detected at each of the N locations in the space at the time point t. Stated differently, the motion localization value $L_{t,n}$ for each of the N individual locations may represent a relative degree of motion detected at the individual location for the time point t. As an example, in the illustration shown in FIG. 3, the element 308 indicates that 8% of the motion was detected by the "Entrance" node (e.g., an AP installed at the home entry) while 62% of the motion was detected by the "Kitchen" node (e.g., an AP installed in the kitchen). In such an example, the motion localization vector $\hat{L}_t$ may indicate that 8% of the motion was detected at the home entry and 62% of the motion was detected in the kitchen.

In some implementations, the degree of motion that occurred at each of the N locations in the space at the time point t can be determined based on the vector $m_t\hat{L}_t=[m_tL_{t,1}\ m_tL_{t,2} \ldots m_tL_{t,N}]$. The pattern extraction engine 508 receives the motion data 514 from the motion detection engine 506 and generates activity data 520 and one or more notifications 522 based on the motion data 514, user input data 524, or both the motion data 514 and the user input data 524. In some instances, the activity data 520 and the one or more notifications 522 are provided for display (e.g., graphical display) on a user interface of a user device.

In some implementations, the activity data 520 may be an actual value for a metric of interest for the time period during which the wireless signals are communicated through the space. The actual value for the metric of interest may be identified based on the motion data 514 received from the motion detection engine 506. In some implementations, the activity data 520 may be a benchmark value for the metric of interest, and the benchmark value for the metric of interest may be identified based on the user input data 524. Various examples of metrics of interest (and examples of actual and benchmark values of such metrics of interest) are discussed in further detail below.

In some implementations, the relative degree of motion detected at an individual location at the time point t depends, at least in part, on the degree of motion detected by the wireless communication device(s) in the individual location at the time point t. For example, in the example of FIG. 2C, the client device 232F is located in the first location 250. Consequently, the degree of motion detected by the client device 232F at the time point t may represent the degree of motion detected in the first location 250 at the time point t.

Similarly, client devices 232A and 232B are located in the second location 252. Consequently, the degree of motion detected by the client device 232A, the client device 232B (or the combined degree of motion detected by both client devices 232A and 232B) at the time point t may represent the degree of motion detected in the second location 252 at the time point t. As another example, client devices 232C, 232D, 232E are located in the third location 254, and the degree of motion detected by each of the client devices 232C, 232D, 232E (or the degree of motion detected by some combination of the client devices 232C, 232D, 232E) at the time point t may represent the degree of motion detected in the third location 254 at the time point t.

In some implementations, the user input data 524 include a time interval $[t_0, t_p]$ within a time period (e.g., the time period 304 shown in FIG. 3) during which the wireless signals are communicated through the space. In some instances, the activity data 520 (e.g., actual value for the metric of interest) can include a measure of the degree of motion that occurred in the space within the time interval $[t_0, t_p]$. In some instances, the measure may be a mean, a median, a mode, a sum, or any other measure that aggregates or averages the degree of motion that occurred in the space within the time interval $[t_0, t_p]$. As an example, the degree of motion may be expressed, in some instances, as a sum, which can be determined as follows:

$$A(t_0, t_p) = \sum_{t_0}^{t_p} m_t.$$

In some implementations, the activity data 520 (e.g., the actual value for the metric of interest) can include the degree of motion that occurred at each of the N locations in the space within the time interval $[t_0, t_p]$. In some instances, the degree of motion that occurred at the $n^{th}$ location within the time interval $[t_0, t_p]$ may be expressed as follows:

$$B_n(t_0, t_p) = \sum_{t_0}^{t_p} m_t L_{t,n}.$$

In some implementations, the activity data 520 (e.g., the actual value for the metric of interest) can include the average degree of motion that occurred at each of the N locations in the space within the time interval $[t_0, t_p]$. In some instances, the average degree of motion that occurred at the $nt^h$ location within the time interval $[t_0, t_p]$ may be expressed as follows:

$$c_n(t_0, t_p) = \frac{1}{(t_p - t_0)} \sum_{t_0}^{t_p} m_t L_{t,n}.$$

In some implementations, the activity data 520 (e.g., the actual value for the metric of interest) can include a determination of which location, among the N locations in the space, experienced the largest degree of motion within the time interval $[t_0, t_p]$. In some instances, the location that experienced the largest degree of motion within the time interval $[t_0, t_p]$ can be determined by determining which location, among the N locations in the space, generated the largest value $B_n(t_0, t_p)$ or the largest value $C_n(t_0, t_p)$.

In some implementations, the activity data 520 (e.g., the actual value for the metric of interest) can include a determination of the number of active minutes at each of the N locations within the time interval $[t_0, t_p]$. As discussed above, the degree of motion that occurred at each of the N locations in the space at the time point t can be determined based on the vector $m_t\widehat{L_t} = [m_tL_{t,1}\ m_tL_{t,2} \ldots m_tL_{t,N}]$. In some instances, the vector $m_t\widehat{L_t}$ for each time point within the time interval $[t_0, t_p]$ can be used to determine the number of active minutes at each of the N locations within the time interval $[t_0, t_p]$. As an example, the vector $m_{t0}\widehat{L_{t0}} = [m_{t0}L_{t0,1}\ m_{t0}L_{t0,2} \ldots m_tL_{t0,N}]$ may represent the degree of motion that occurred at each of the N locations in the space at the time point $t_0$; the vector $m_{t1}\widehat{L_{t1}} = [m_{t1}L_{t1,1}\ m_{t1}L_{t1,2} \ldots m_{t1}L_{t1,N}]$ may represent the degree of motion that occurred at each of the N locations in the space at the time point $t_1$; and so on. In some implementations, the entries of each of the vectors $m_{t0}\widehat{L_{t0}}, m_{t1}\widehat{L_{t1}}, \ldots, m_{tp}\widehat{L_{tp}}$ may be grouped to the nearest minute, and a non-zero entry may be indicative of an active minute (e.g., a minute in which there is a non-zero degree of motion). For each location across the vectors $m_{t0}\widehat{L_{t0}}$, $m_{t1}\widehat{L_{t1}}, \ldots, m_{tp}\widehat{L_{tp}}$, the number of active minutes at a given location within the time interval $[t_0, t_p]$ can be determined by adding number of non-zero entries for that given location across the vectors $m_{t0}\widehat{L_{t0}}$, $m_{t1}\widehat{L_{t1}}, \ldots, m_{tp}\widehat{L_{tp}}$. In some instances, the number of active minutes may be expressed as a percentage (e.g., relative to the number of minutes in the time interval $[t_0, t_p]$). In some implementations, the activity data 520 can include a determination of the number of inactive minutes at each of the N locations within the time interval $[t_0, t_p]$. For example, the entries of each of the vectors $m_{t0}\widehat{L_{t0}}$, $m_{t1}\widehat{L_{t1}}, \ldots, m_{tp}\widehat{L_{tp}}$ may be grouped to the nearest minute, and a zero entry may be indicative of an inactive minute (e.g., a minute in which there is no degree of motion detected). For each user location across the vectors $m_{t0}\widehat{L_{t0}}$, $m_{t1}\widehat{L_{t1}}, \ldots, m_{tp}\widehat{L_{tp}}$, the number of inactive minutes at a given location within the time interval $[t_0, t_p]$ can be determined by adding the number of zero entries for that given location across the vectors $m_{t0}\widehat{L_{t0}}$, $m_{t1}\widehat{L_{t1}}, \ldots, m_{tp}\widehat{L_{tp}}$. In some instances, the number of inactive minutes may be expressed as a percentage (e.g., relative to the number of minutes in the time interval $[t_0, t_p]$).

In some implementations, the user input data 524 can include a time interval $[t_{s1}, t_{s2}]$ within a time period (e.g., the time period 304 shown in FIG. 3) during which the wireless signals are communicated through the space. The time interval $[t_{s1}, t_{s2}]$ may be indicative of a time interval during which a person expects to be asleep. The user input data can also include a targeted duration of sleep during the time interval $[t_{s1}, t_{s2}]$. Given the time interval $[t_{s1}, t_{s2}]$ and the targeted duration of sleep during the time interval $[t_{s1}, t_{s2}]$, the activity data 520 (e.g., the actual value for the metric of interest) can include one or more of the following: a total duration of sleep observed during the time interval $[t_{s1}, t_{s2}]$; a total duration of movement observed during the time interval $[t_{s1}, t_{s2}]$; a degree of motion observed for each time point within the time interval $[t_{s1}, t_{s2}]$; or sleep levels observed during the time interval $[t_{s1}, t_{s2}]$. In some instances, the activity data 520 (e.g., the benchmark value for the metric of interest) can include the targeted duration of sleep during the time interval $[t_{s1}, t_{s2}]$.

In some implementations, the total duration of movement observed during the time interval $[t_{s1}, t_{s2}]$ can be obtained by determining the number of active minutes at the sleeping location within the time interval $[t_{s1}, t_{s2}]$ and, as discussed above, the number of active minutes at a given location (e.g., the sleeping location) within the time interval $[t_{s1}, t_{s2}]$ can be determined by adding the number of non-zero entries for the sleeping location across the vectors $m_{t_{s1}}\widehat{L_{t_{s1}}}, \ldots, m_{t_{s2}}\widehat{L_{t_{s2}}}$.

In some implementations, the degree of motion observed for each time point within the time interval $[t_{s1}, t_{s2}]$ can be obtained based on the vector $[m_{t_{s1}}L_{t_{s1},i} \ldots m_{t_{s2}}L_{t_{s2},i}]$, where the $i^{th}$ location is the sleeping location.

In some implementations, the sleep levels observed during the time interval $[t_{s1}, t_{s2}]$ can include an indication of durations of restful sleep within the time interval $[t_{s1}, t_{s2}]$; an indication of durations of light sleep within the time interval $[t_{s1}, t_{s2}]$; and an indication of durations of disrupted sleep within the time interval $[t_{s1}, t_{s2}]$.

Figure 6A:
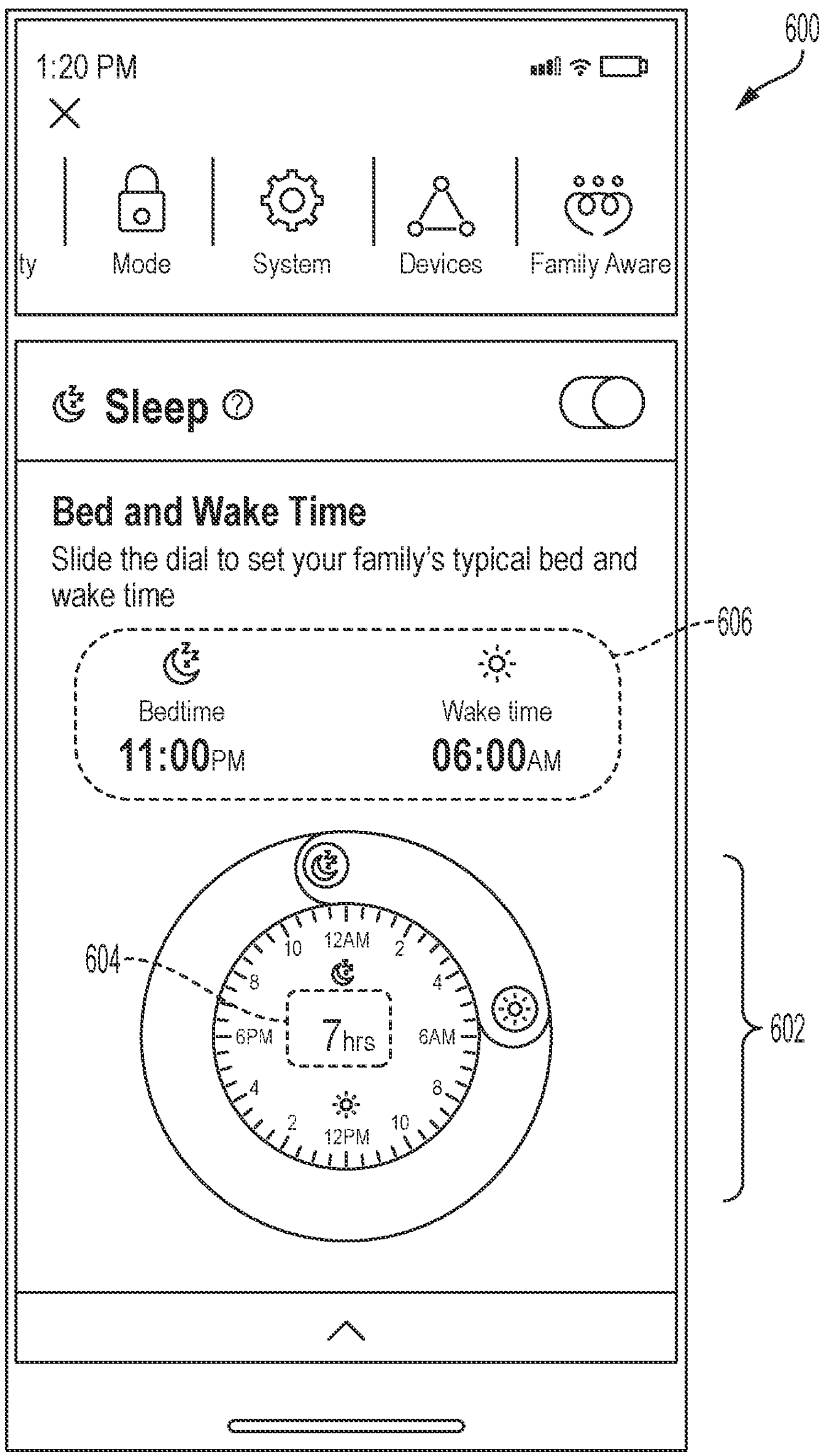
FIG. 6A is a diagram showing an example user interface that allows a user to select a time interval indicative of a bedtime and a wake time.

FIG. 6A is a diagram showing an example user interface 600 that allows a user to select a time interval indicative of a bedtime and a wake time. The example user interface 600 includes a selection element 602 that a user can interact with to select an expected bedtime and an expected wake time. The selection element 602 can be displayed as a dial, although other manners of displaying the selection element 602 are possible. In the example shown in FIG. 6A, the expected bedtime is selected as 11:00 PM and the expected wake time is selected as 6:00 AM. In some instances, such as in the example shown in FIG. 6A, the user interface 600 includes an element 604 that indicates the total sleep duration (e.g., determined based on the expected bedtime and expected wake time), and an element 606 that summarizes the selection made by the user.

Figure 6B:
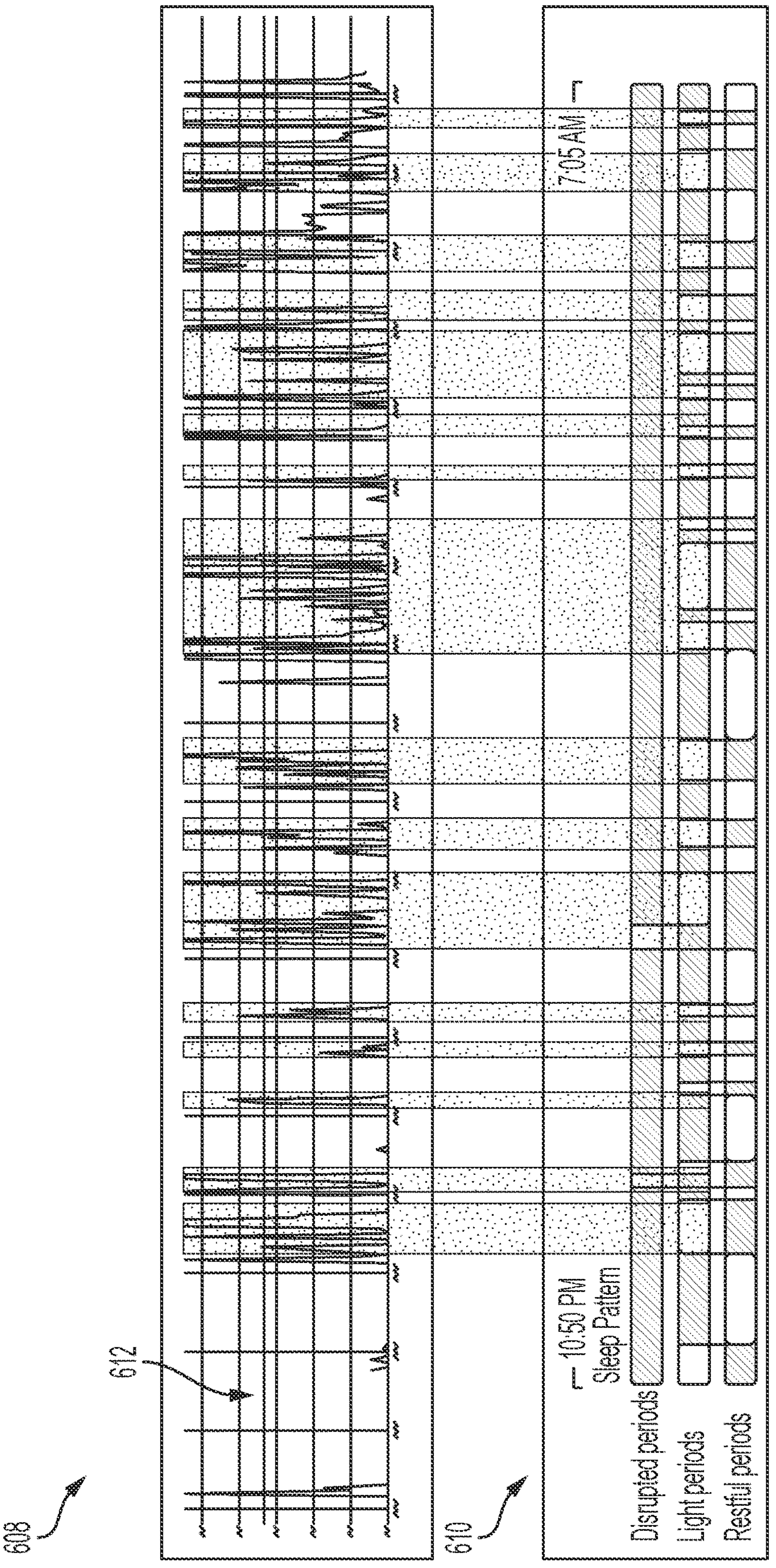
FIG. 6B is a diagram showing a plot of a degree of motion as a function of time and a plot showing corresponding periods of disrupted, light, and restful sleep.

FIG. 6B is a diagram showing a plot 608 of motion data as a function of time and a plot 610 showing corresponding periods of disrupted, light, and restful sleep. The example data shown in FIG. 6B can be provided, for example, by the wireless communication device 400 shown in FIG. 4 or by another type of system or device. The horizontal axis in plot 608 represents time (e.g., the time interval $[t_{s1}, t_{s2}]$ including multiple time points), and the vertical axis represents the degree of motion detected at each time point. The threshold 612 represents a maximum degree of motion that is indicative of restful sleep. The horizontal axis in plot 610 represents time (e.g., the time interval $[t_{s1}, t_{s2}]$ including multiple time points) and corresponds to the horizontal axis in the plot 608. In plot 610, three types of sleep patterns are identified: "Disrupted periods", "Light periods" and "Restful periods". Other types of sleep patterns may be used. The degree of motion in the plot 608 is used to classify time segments in one of the three sleep patterns. For example, consistent durations with no significant motion above threshold 612 map to "Restful periods," motion above the threshold 612 for less than a predetermined duration map to "Light periods," and motion above threshold 612 for greater than a predetermined duration map to "Disrupted periods."

As an illustration, the person may lie on a bed and place the wireless communication device 400 on a nightstand. The wireless communication device 400 may determine the degree of motion while the person is lying in bed (e.g., based on channel information obtained from wireless signals transmitted in the space in which the person is sleeping). In some implementations, a low degree of motion may be inferred when the degree of motion is less than a first threshold, and a high degree of motion may be inferred when the degree of motion is greater than a second threshold. As an example, turning or repositioning in the bed can produce a smaller degree of motion over a first duration of time (e.g., between 1 and 5 seconds) compared to instances when the person is walking, which may produce a greater degree of motion over a second (longer) duration of time. In some instances (e.g., the example shown in FIG. 6B), the first threshold may be equal to the second threshold, although in other examples the second threshold is greater than the first threshold. In some implementations, the thresholds that are selected can be based on one or more factors, including the degree of the motion that is detected and the duration of the motion that is detected. Furthermore, the thresholds can be selected after user-trials and can also be adjusted automatically by the application that is using the motion detection system on a per-user basis by observing typical over-night behavior of the person.

Periods during which the degree of motion is less than the threshold 612 may indicate periods of restful sleep (e.g., deep sleep or REM sleep). The person may toss and turn while sleeping, and the wireless communication device 400 can detect the degree of motion of the person. Periods during which the degree of motion is greater than the threshold 612 may indicate either that the person has woken from sleep or that the person is having a period of disrupted, restless sleep or light sleep. Short bursts of motion occurring after sleep monitoring has commenced may indicate periods of disrupted, restless sleep or light sleep. In some implementations, periods of disrupted, restless sleep or light sleep are detected when the degree of motion is greater than the threshold 612 for a first predetermined duration of time (e.g., less than 5 seconds, or another duration). Conversely, prolonged bursts of motion occurring after sleep monitoring has commenced may indicate that the person has woken from sleep. In some implementations, the wireless communication device 400 determines that the person is awake when the degree of motion is greater than the threshold 612 for a second predetermined duration of time (e.g., more than 5 seconds, or another duration). In some implementations, the first and second predetermined durations of time may be functions of the degree of motion detected. For example, a longer duration of time may be associated with a low degree of motion, and a shorter duration of time may be associated with a high degree of motion to distinguish between the light (rapid eye movement) sleep state and the disrupted sleep (awake) state.

Figure 6C:
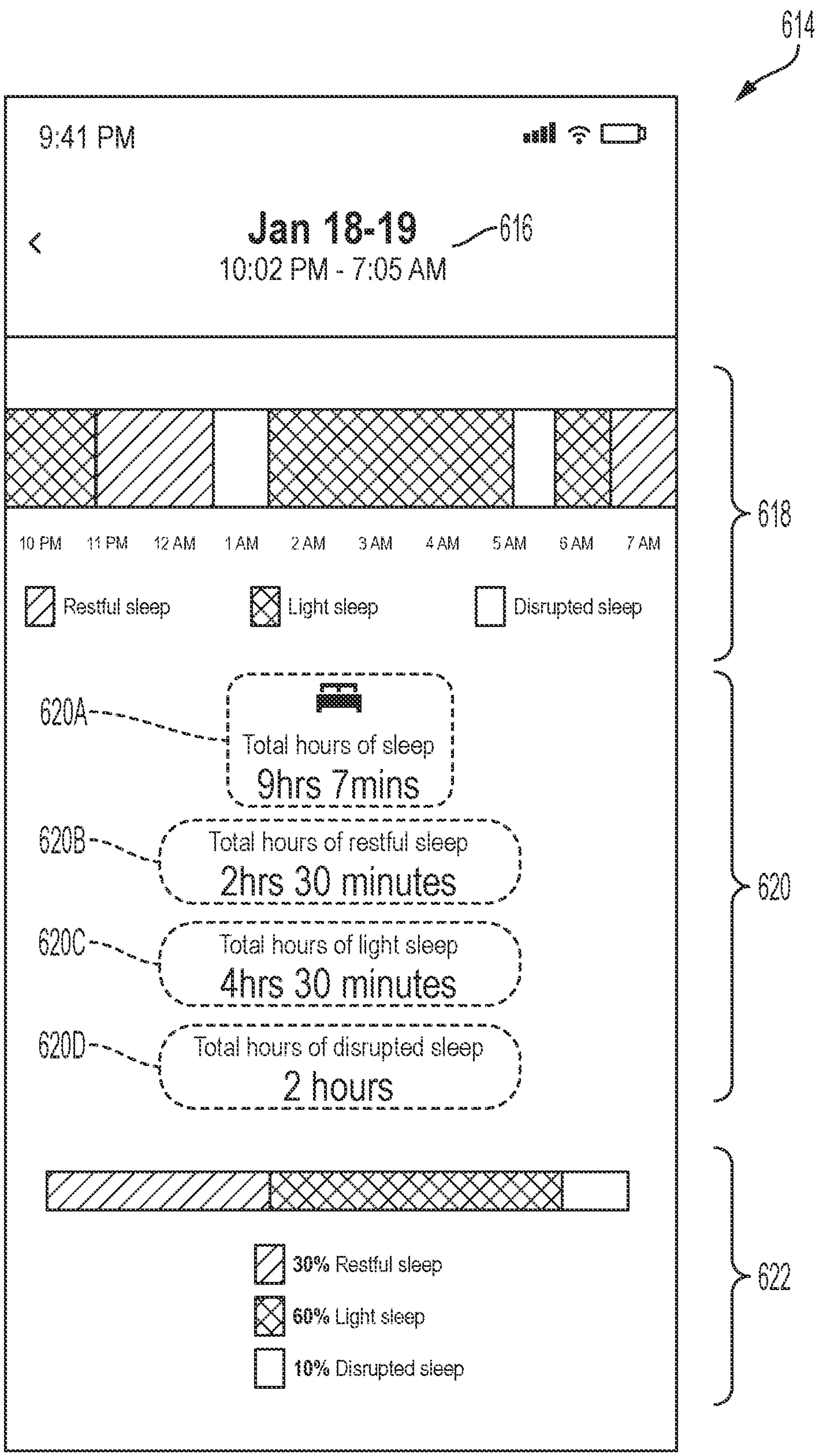
FIG. 6C is a diagram showing an example user interface that displays periods of disrupted, light, and restful sleep.

The plots 608 and 610 are one example of showing corresponding periods of disrupted, light, and restful sleep. FIG. 6C is a diagram showing an example user interface 614 that displays periods of disrupted, light, and restful sleep. The user interface 614 illustrates another example of showing corresponding periods of disrupted, light, and restful sleep. The user interface 614 includes an element 616 that displays the time interval $[t_{s1}, t_{s2}]$ (e.g., the time interval during which a person is, or expects to be, asleep) and the date(s) spanned by the time interval $[t_{s1}, t_{s2}]$. The example user interface 614 also includes a plot 618 showing corresponding periods of disrupted, light, and restful sleep. The horizontal axis in plot 618 represents time (e.g., the time interval $[t_{s1}, t_{s2}]$ including multiple time points). The example user interface 614 further includes an element 620 that displays the total amount of sleep 620A (e.g., obtained based on the total duration of the time interval $[t_{s1}, t_{s2}]$). The element 620 also displays the total duration of restful sleep 620B, the total duration of light sleep 620C, and the total duration disrupted sleep 620D within the time interval $[t_{s1}, t_{s2}]$. In some instances, such as in the example shown in FIG. 6C, the user interface 614 includes element 622 that displays statistical information related to the time interval $[t_{s1}, t_{s2}]$. As an example, the element 622 displays the total duration of restful sleep, light sleep, and disrupted sleep as percentages of the total amount of sleep.

The sleeping behavior (e.g., sleep quality) can be determined based on the level of motion during the time interval $[t_{s1}, t_{s2}]$. For example, in some implementations, a metric indicative of sleep quality can be determined based on a ratio of a total duration of the periods of restful sleep to the total duration of sleep monitoring (e.g., obtained from the starting and ending times in the time interval $[t_{s1}, t_{s2}]$).

In some implementations, the total duration of sleep observed during the time interval $[t_{s1}, t_{s2}]$ can be determined based on the sleep levels observed during the time interval $[t_{s1}, t_{s2}]$. For example the total duration of sleep observed during the time interval $[t_{s1}, t_{s2}]$ can be based on the total duration of restful sleep within the time interval $[t_{s1}, t_{s2}]$ or a sum of the durations of restful sleep and light sleep within the time interval $[t_{s1}, t_{s2}]$, although other methods of determining the total duration of sleep observed during the time interval $[t_{s1}, t_{s2}]$ may be used.

In some implementations, the user input data 524 include a time interval $[t_{a1}, t_{a2}]$ within a time period (e.g., the time period 304 shown in FIG. 3) during which the wireless signals are communicated through the space. The time interval $[t_{a1}, t_{a2}]$ may be indicative of a time interval during which a person expects to be awake. The user input data can also include a targeted duration of movement during the time interval $[t_{a1}, t_{a2}]$. Given the time interval $[t_{a1}, t_{a2}]$ and the targeted duration of movement during the time interval $[t_{a1}, t_{a2}]$, the activity data 520 (e.g., the actual value for the metric of interest) can include one or more of the following: a total duration of movement observed during the time interval $[t_{a1}, t_{a2}]$; a degree of motion observed at each location for each time point within the time interval $[t_{a1}, t_{a2}]$; or the location exhibiting the highest degree of motion during the time interval $[t_{a1}, t_{a2}]$. In some instances, the activity data 520 (e.g., the benchmark value for the metric of interest) include the targeted duration of movement during the time interval $[t_{a1}, t_{a2}]$.

In some instances, the user input data 524 include a time interval $[t_{n1}, t_{n2}]$ within a time period (e.g., the time period 304 shown in FIG. 3) during which the wireless signals are communicated through the space. The time interval $[t_{n1}, t_{n2}]$ may be indicative of a time interval during which motion is not expected in the space or in one or more locations within the space. In some instances, the pattern extraction engine 508 may determine, based on the user input data 524 and the motion data 514, that motion has occurred in at least one location in the space during the time interval $[t_{n1}, t_{n2}]$. In such instances, the pattern extraction engine 508 may generate a notification 522 (e.g., for display on a user interface of a user device) that motion has occurred within the time interval $[t_{s1}, t_{s2}]$ during which motion was not expected.

In some instances, the user input data 524 include an indication of one or more locations within the space at which motion is not expected. For example, the user input data 524 may include an indication that motion is not expected in the kitchen area. In some instances, the pattern extraction engine 508 may determine, based on the user input data 524 and the motion data 514, that motion has occurred in at least one of the locations specified by the user input data 524. In such instances, the pattern extraction engine 508 may generate a notification 522 (e.g., for display on a user interface of a user device) that motion has occurred at one or more of the locations at which motion was not expected.

In some instances, the user input data 524 include notification times designated by a user. The notification times may be times at which the one or more notifications 522 may be generated by the pattern extraction engine 508. In an event that the current time is not one of notification times designated by the user, the pattern extraction engine 508 may forgo generating the one or more notifications 522. In some instances, the user input data 524 include an indication of motion events for which the user would like to receive notifications 522. In an instance where the motion event is not one of events designated by the user, the pattern extraction engine 508 may forgo generating the one or more notifications 522.

In addition to the examples discussed above, the notification(s) 522 can include at least one of the following: one or more of the metrics of interest discussed above; an indication of an operating state of the motion detection system 500 (e.g., an indication that the motion detection system 500 was set to an Away or Home mode); an indication of a geofence event (e.g., an indication that a person has left the space or a location in the space); an activity alert (e.g., an indication that a person is not yet awake, an indication that no motion has been detected for a stated period of time, an indication of the number of times a person arose from sleep last night, etc.); or any other type of notification that conveys information about the motion detection system 500 or about motion that was detected in a space.

Figure 7:
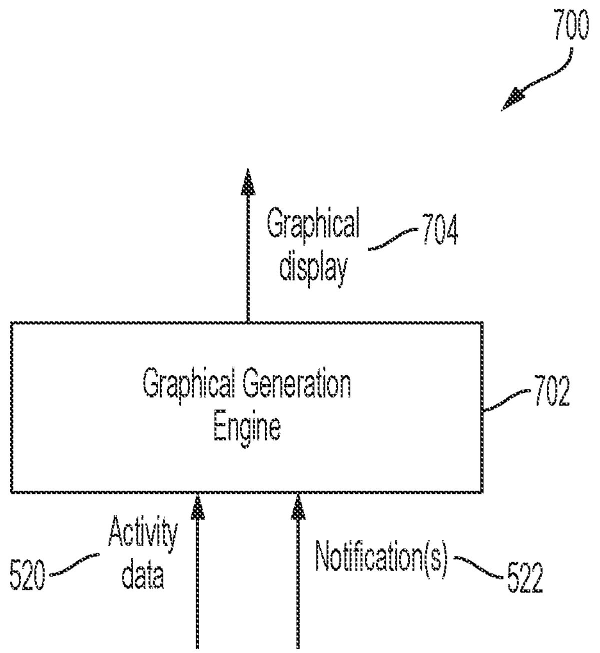
FIG. 7 is a block diagram showing an example system for generating a graphical display based on activity data and at least one notification.

FIG. 7 is a block diagram showing an example system 700 for generating a graphical display based on activity data and at least one notification. The system 700 may be included in a user device or another type of system or device. In some implementations, the user device is the client device 232 shown in FIG. 2C, a user device of a caregiver or emergency contact designated to an individual in the space 200, 201, or any other user device that is communicatively coupled to receive the activity data 520 and the one or more notifications 522 from the system 500.

The system 700 includes a graphical generation engine 702 that generates a graphical display 704 based on the activity data 520 and the one or more notifications 522. As discussed above, in some instances, the activity data 520 may include one or more of the following: a total duration of sleep observed during the time interval $[t_{s1}, t_{s2}]$; a total duration of movement observed during the time interval $[t_{s1}, t_{s2}]$; a degree of motion observed for each time point within the time interval $[t_{s1}, t_{s2}]$; sleep levels observed during the time interval $[t_{s1}, t_{s2}]$; or the targeted duration of sleep during the time interval $[t_{s1}, t_{s2}]$. In such instances, the graphical display 704 that is generated by the graphical generation engine 702 may be a graphic that displays the total duration of sleep observed during the time interval $[t_{s1}, t_{s2}]$ (e.g., relative to the targeted duration of sleep during the time interval $[t_{s1}, t_{s2}]$). Additionally or alternatively, the graphical display 704 that is generated by the graphical generation engine 702 may be a graphic that displays a total duration of movement observed during the time interval $[t_{s1}, t_{s2}]$, a degree of motion observed for each time point within the time interval $[t_{s1}, t_{s2}]$, the sleep levels observed during the time interval $[t_{s1}, t_{s2}]$, or a combination thereof.

As discussed above, in some instances, the activity data 520 may include one or more of the following: a total duration of movement observed during the time interval $[t_{a1}, t_{a2}]$; a degree of motion observed at each location for each time point within the time interval $[t_{a1}, t_{a2}]$; the location exhibiting the highest degree of motion during the time interval [$t_{a1}$, $t_{a2}$]; or the targeted duration of movement during the time interval [$t_{a1}$, $t_{a2}$].

In such instances, the graphical display 704 that is generated by the graphical generation engine 702 may be a graphic that displays the total duration of movement observed during the time interval [$t_{a1}$, $t_{a2}$] (e.g., relative to the targeted duration of movement during the time interval [$t_{a1}$, $t_{a2}$]). Additionally or alternatively, the graphical display 704 that is generated by the graphical generation engine 702 may be a graphic that displays the degree of motion observed at each location for each time point within the time interval [$t_{a1}$, $t_{a2}$], the location exhibiting the highest degree of motion during the time interval [$t_{a1}$, $t_{a2}$], or a combination thereof.

Figure 8A:
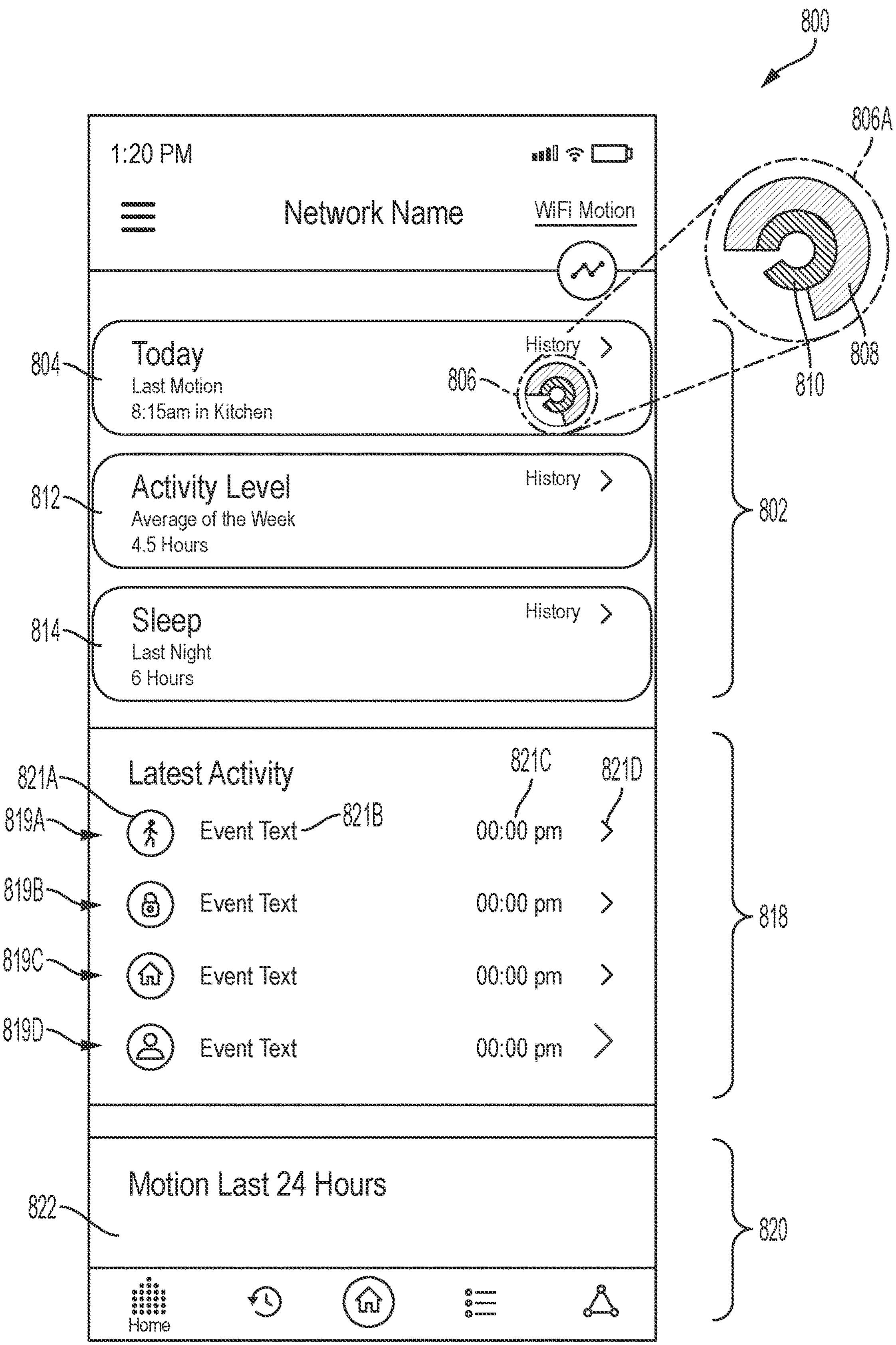
FIGS. 8A to 8H show example graphical displays that may be generated by the system shown in FIG. 7.
Figure 8B:
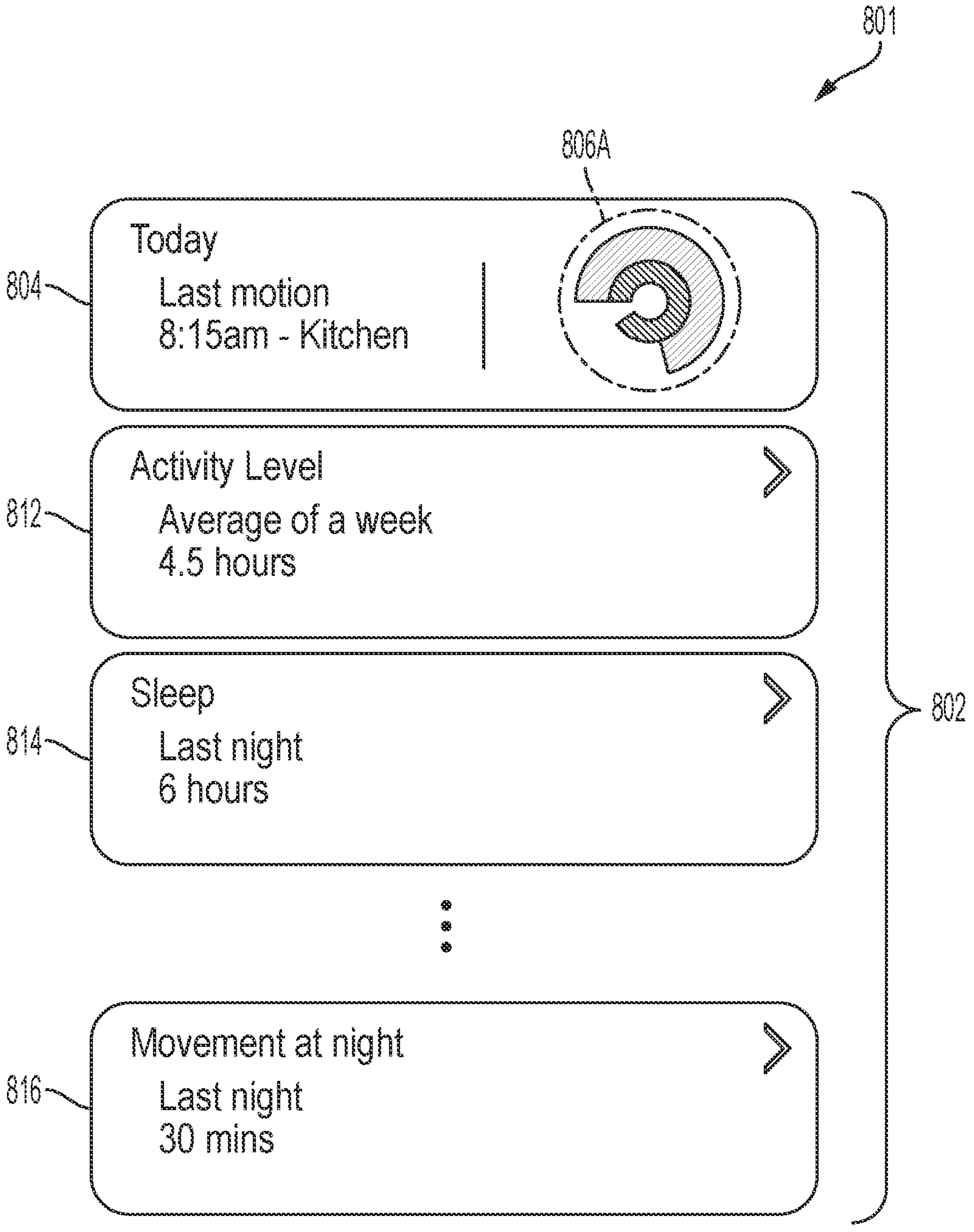

FIGS. 8A to 8H show examples of graphical displays that may be generated by the system 700 shown in FIG. 7. In FIG. 8A, the example graphical display 800 includes an element 802 that displays one or more tiles 804, 812, 814, each corresponding to a respective metric of interest. In the example shown in FIG. 8A, a first tile 804 is a summary of motion and sleep for the day. In some instances, a chart 806A can display (e.g., simultaneously display) the duration of movement for the day (indicated by circular chart 808) and the duration of sleep for the day (indicated by circular chart 810). The element 802 shown in the example of FIG. 8A also displays a second tile 812, which is a summary of activity levels over a timeframe (e.g., a week in the example of FIG. 8A). The element 802 also displays a third tile 814, which is a summary of sleep levels over a timeframe (e.g., the night before in the example of FIG. 8A). The number of tiles displayed by element 802 can be configured based on user preferences (e.g., which may be provided to the graphical generation engine 702). As an example, FIG. 8B shows an example graphical display 801 where the element 802 additionally displays a tile 816, which is a summary of movement over a time frame (e.g., the night before in the example of FIG. 8B).

The example graphical display 800 in FIG. 8A also includes an element 818 that displays one or more of the notifications 522 generated by the motion detection system. In some instances, such as in the example of FIG. 8A, the notifications 522 can be displayed as a list of row elements 819A, 819B, 819C, 819D. The list of row elements 819A to 819D can be ordered in any way, one example being a reverse chronological order, where the most recent notification is displayed at the top of the list. Each row element 819 includes a respective icon, text, and timestamp. As an example, row element 819A includes a respective icon 821A, title 821B, and timestamp 821C. In some instances, the icon 821A and title 821B are descriptive of the metric of interest that the row element 819A is associated with. The timestamp 821C indicates the time at which the metric of interest (e.g., described by the icon 821A and the title 821B) was detected. In some instances, the timestamp 821C can be informed by the motion data 514, user input data 524, or both. In some instances, each row element 819 includes a respective menu element (e.g., row element 819A includes menu element 821D). The menu element 821D can be selected by the user to reveal further details associated with the metric of interest indicated by row element 819A. The example graphical display 800 in FIG. 8A further includes an element 820 that displays a selectable menu 822 that allows a user to obtain information on additional metrics of interest (e.g., motion in the last 24 hours in the example of FIG. 8A).

Figure 8C:
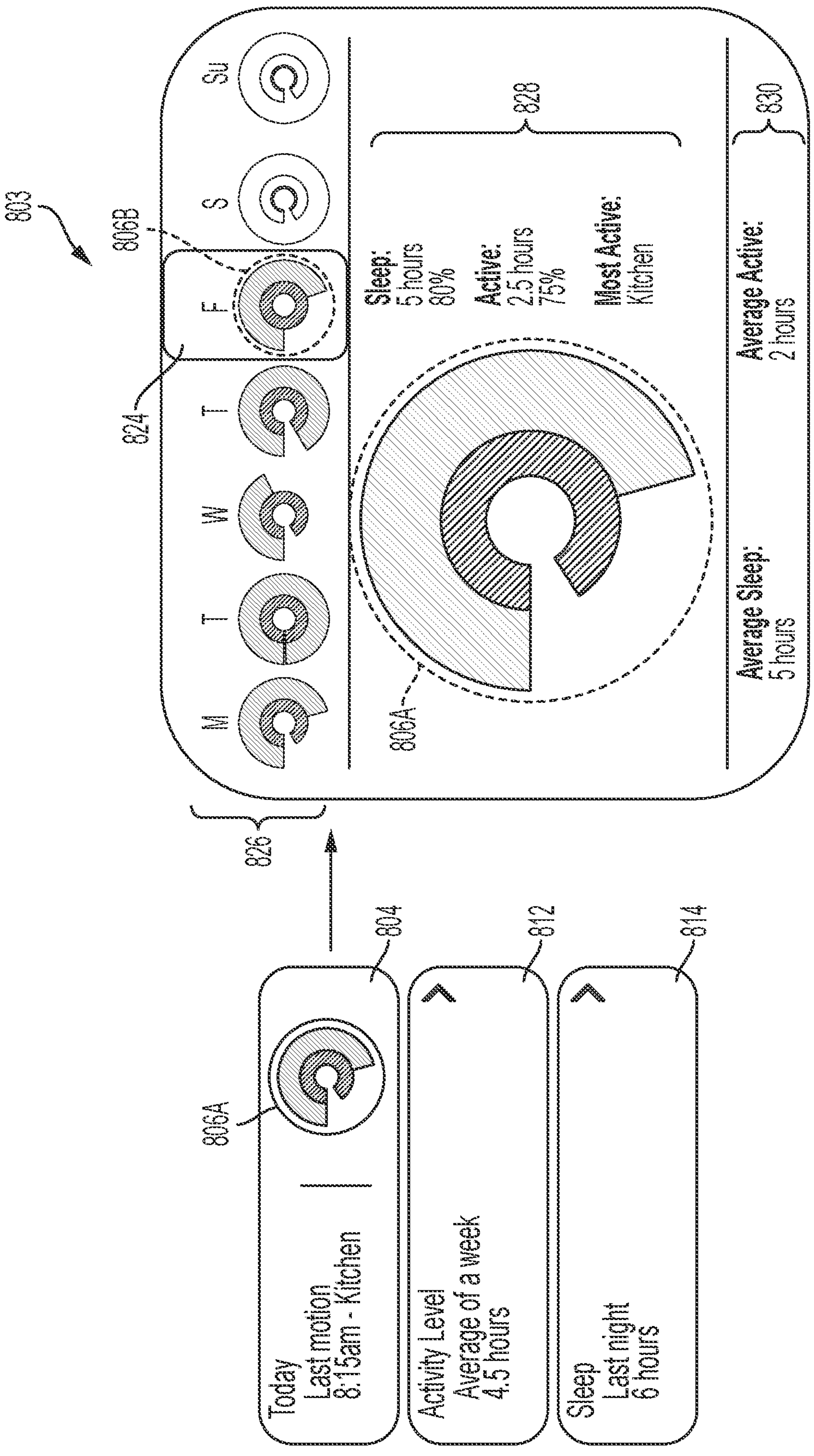

Each tile can be expanded to display further metrics of interest. FIG. 8C shows an example graphical display 803 where the first tile 804 is selected by a user (e.g., by the user's finger touch on the user device's touch screen). The graphical display 803 includes the chart 806B and an indication 824 of which day of the week the chart 806B corresponds to. The graphical display 803 also includes an element 826 that displays a summary of motion and sleep for each day of the week, where each day of the week has a respective chart that displays (e.g., simultaneously displays) the duration of movement for the respective day (indicated by the outer circular chart) and the duration of sleep for the respective day (indicated by the inner circular chart). For the day highlighted by the indication 824, the graphical display 803 also includes elements 828 and 830 that provide further details related to the day's chart 806B. The user can select the chart 806B for any day illustrated in element 826 to display elements 828 and 830 that provide further details related to the day's chart 806B.

In some implementations, the graphical display 803 includes element 828 that displays numerical values for the total duration of movement observed for the day (e.g., indicated as 2.5 hours in the example of FIG. 8C) and the total duration of sleep observed for the day (e.g., indicated as 5 hours in the example of FIG. 8C). In some instances (such as in the example of FIG. 8C), the numerical values include a percentage that indicates the total duration of movement observed for the day relative to the targeted duration of movement for the day (e.g., indicated as 75% in the example of FIG. 8C) or a percentage that indicates the total duration of sleep observed for the day relative to the targeted duration of sleep for the day (e.g., indicated as 80% in the example of FIG. 8C). The element 828 may display an indication of the most active location in the space for the day (e.g., indicated as the kitchen in the example of FIG. 8C).

In some implementations, the graphical display 803 includes element 830 that displays an average duration of sleep observed for the week (e.g., indicated as 5 hours in the example of FIG. 8C) or an average duration of movement for the week (e.g., indicated as 2 hours in the example of FIG. 8C).

Figure 8D:
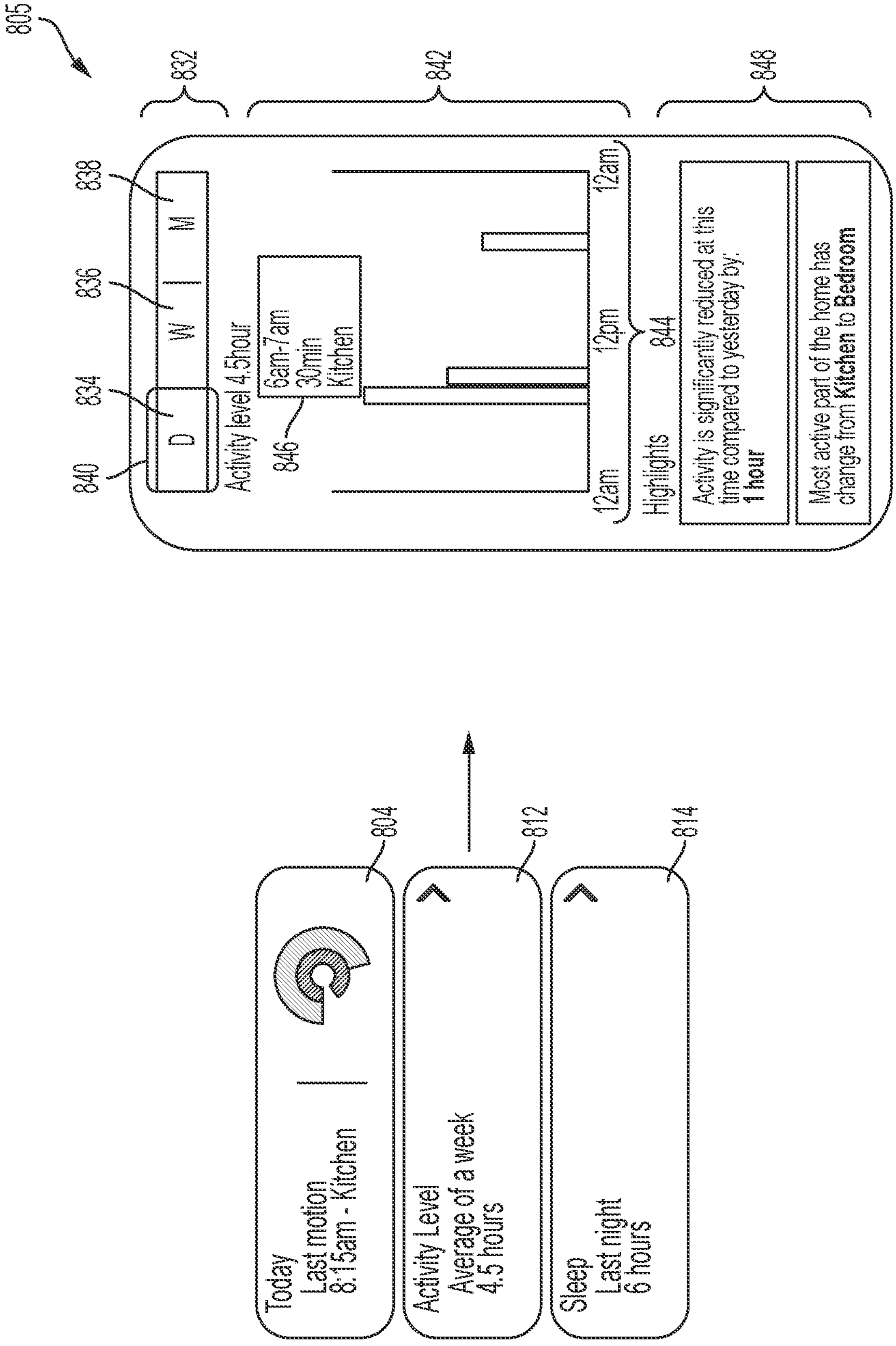

FIG. 8D shows an example graphical display 805 where the second tile 812 is selected by a user (e.g., by the user's finger touch on the user device's touch screen). As discussed above, the second tile 812 is a summary of activity levels over a timeframe (e.g., a week in the example of FIG. 8A). The graphical display 805 includes an element 832 that allows the user to select a particular timeframe from a plurality of timeframes. In the example of FIG. 8D, the plurality of timeframes include a timeframe of a day 834, a timeframe of a week 836, and a timeframe of a month 838. The plurality of timeframes indicated by element 832 is not limited to a day, a week, or a month, and in other instances of the element 832, the timeframes can be any time period (e.g., based on a choice by the user, which can be informed by user input data 524). The element 832 also displays an indication 840 of which timeframe is currently selected. The graphical display 805 further includes an element 842 that includes a horizontal timeline that includes a time period 844 (including a series of time points) and a plot of motion data indicating a degree of motion detected by the motion detection system for each time point in the time period 844. In the example shown in FIG. 8D, the timeframe selected is a day 834, and consequently, the time period 844 displayed is a 24-hour period. In some implementations, each time point in the time period 844 may represent an hour within the 24-hour period. In some instances, the element 842 displays information 846 related to the degree of motion detected in response to the user selecting the degree of motion (e.g., by the user's finger touch on the user device's touch screen). For example, the information 846 may indicate the location of the motion detected (e.g., the kitchen in the example of FIG. 8D), a time interval in which the motion was detected (e.g., between 6 am and 7 am in the example of FIG. 8D), and a duration of the motion (e.g., 30 minutes in the example of FIG. 8D). The graphical display 805 further includes element 848 that displays a comparison of current motion data with previous motion data. In some instances, the comparison indicates a change in the duration of motion over a timeframe (e.g., from one day to the next), a change in the location that experienced the largest degree of motion (e.g., from one day to the next), or both.

Figure 8E:
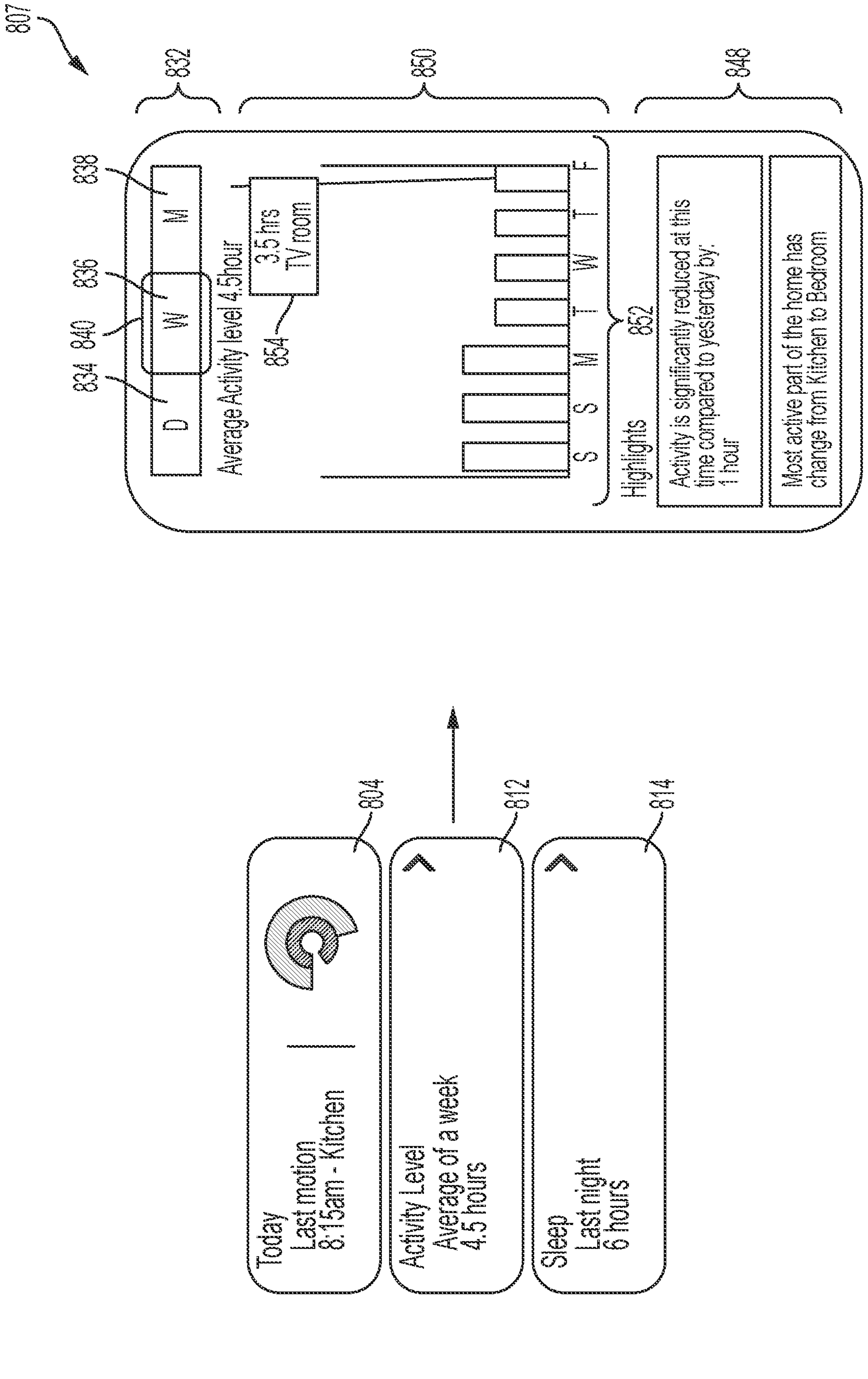

FIG. 8E shows an example graphical display 807 where the second tile 812 is selected by a user (e.g., by the user's finger touch on the user device's touch screen) and where the timeframe selected by the user is a week 836. In contrast to the graphical display 805 shown in FIG. 8D, the graphical display 807 includes an element 850 that includes a horizontal timeline that includes a time period 852 (including a series of time points) and a plot of motion data indicating a degree of motion detected by the motion detection system for each time point in the time period 852. In the example shown in FIG. 8E, the timeframe selected is a week 836, and consequently, the time period 852 displayed is a one-week period. In some implementations, each time point in the time period 852 may represent a day within the one-week period. In some instances, the element 850 displays information 854 related to the degree of motion detected in response to the user selecting the degree of motion (e.g., by the user's finger touch on the user device's touch screen). For example, the information 854 may indicate the location of the motion detected (e.g., the TV room in the example of FIG. 8E) and a duration of the motion (e.g., 3.5 hours in the example of FIG. 8E).

Figure 8F:
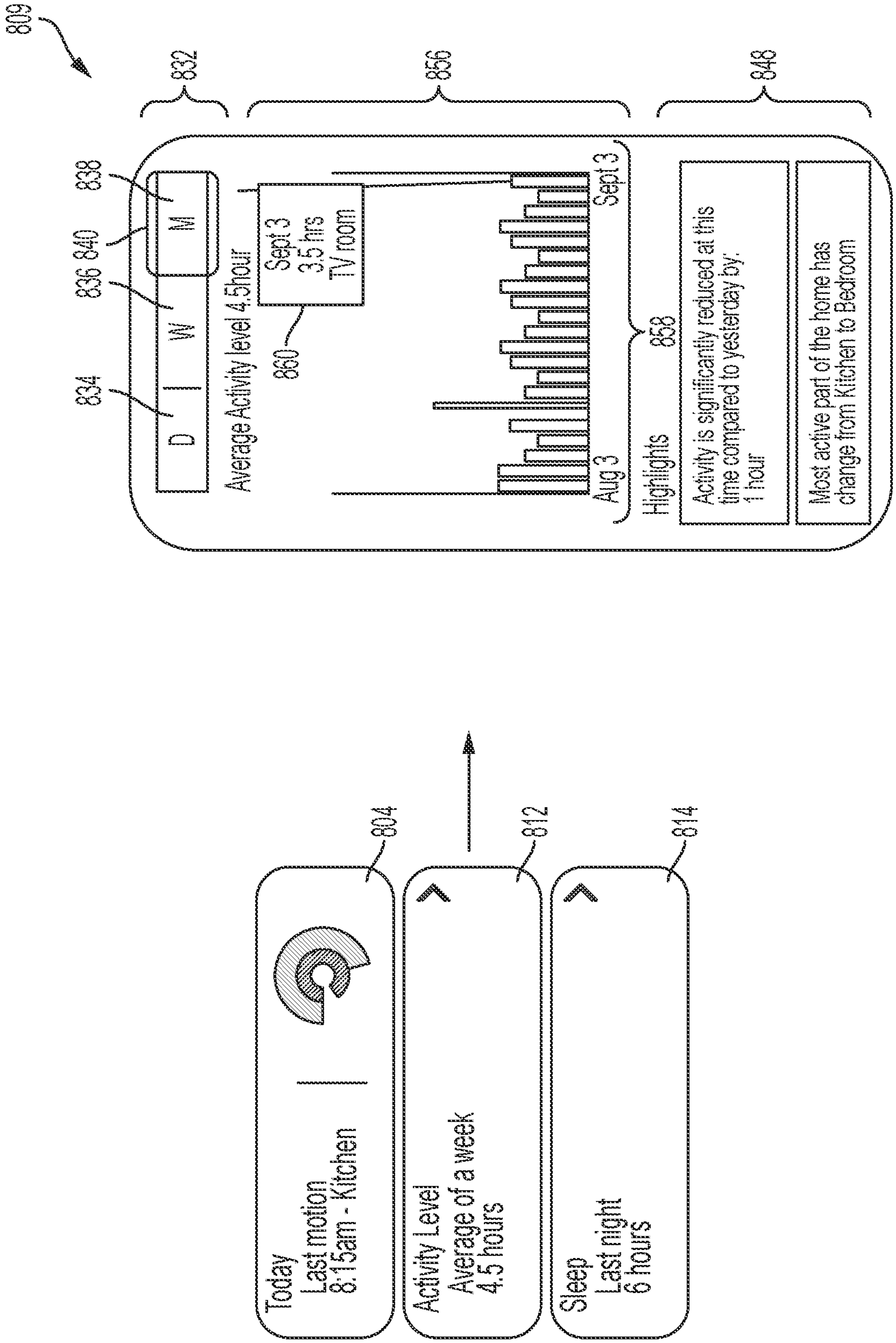

FIG. 8F shows an example graphical display 809 where the second tile 812 is selected by a user (e.g., by the user's finger touch on the user device's touch screen) and where the timeframe selected by the user is a month 838. In contrast to the graphical display 807 shown in FIG. 8E, the graphical display 809 includes an element 856 that includes a horizontal timeline that includes a time period 858 (including a series of time points) and a plot of motion data indicating a degree of motion detected by the motion detection system for each time point in the time period 858. In the example shown in FIG. 8F, the timeframe selected is a month 838, and consequently, the time period 858 displayed is a one-month period. In some implementations, each time point in the time period 858 may represent a day within the one-month period. In some instances, the element 856 displays information 860 related to the degree of motion detected in response to the user selecting the degree of motion (e.g., by the user's finger touch on the user device's touch screen). For example, the information 860 may indicate the location of the motion detected (e.g., the TV room in the example of FIG. 8F), the time point at which the motion was detected (e.g., September 3 in the example of FIG. 8F), and a duration of the motion (e.g., 3.5 hours in the example of FIG. 8F).

Figure 8G:
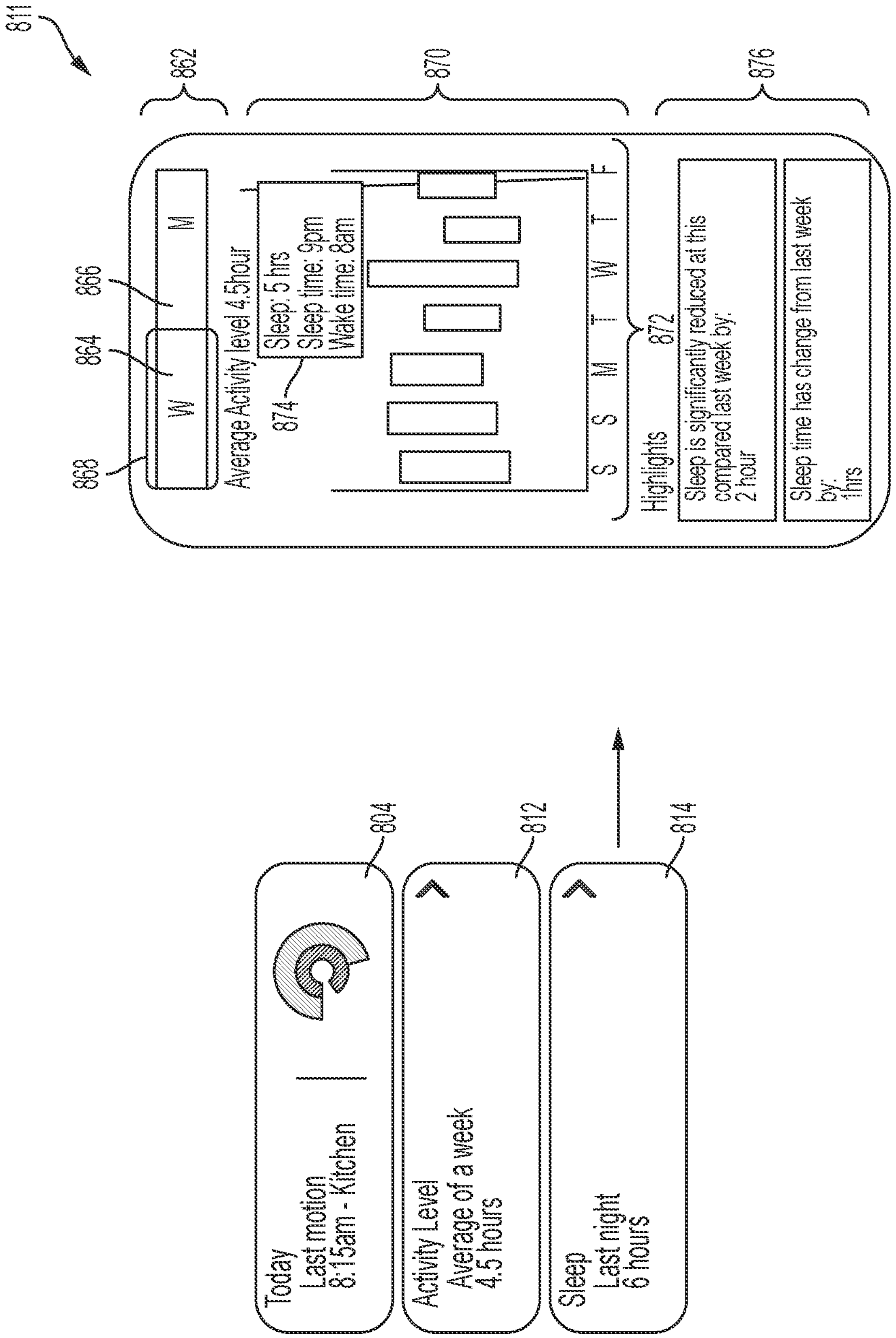

FIG. 8G shows an example graphical display 811 where the third tile 814 is selected by a user (e.g., by the user's finger touch on the user device's touch screen). As discussed above, the third tile 814 is a summary of sleep levels over a timeframe (e.g., the night before in the example of FIG. 8A). The graphical display 811 includes an element 862 that allows the user to select a particular timeframe from a plurality of timeframes. In the example of FIG. 8G, the plurality of timeframes includes a timeframe of a week 864 and a timeframe of a month 866. The element 862 also displays an indication 868 of which timeframe is currently selected. The graphical display 811 further includes an element 870 that includes a horizontal timeline that includes a time period 872 (including a series of time points) and a plot of sleep data indicating activity data related to sleep, for each time point in the time period 872. In the example shown in FIG. 8G, the timeframe selected is a week 864, and consequently, the time period 872 displayed is a one-week period. In some implementations, each time point in the time period 872 may represent a day within the one-week period. In some instances, the element 870 displays information 874 related to the activity data related to sleep, in response to the user selecting the sleep data (e.g., by the user's finger touch on the user device's touch screen). For example, the information 874 may indicate a total duration of sleep observed during the time point (e.g., 5 hours in the example of FIG. 8G), a time at which sleep commenced (e.g., 9 pm in the example of FIG. 8G), and a time at which sleep concluded (e.g., 8 am in the example of FIG. 8G). In some instances, element 870 displays other information related to sleep (e.g., the sleep state at various durations during the night, example sleep states being restless sleep, light sleep, and deep or REM sleep). The graphical display 811 further includes element 876 that displays a comparison of current sleep data with previous sleep data. In some instances, the comparison may indicate a change in the total duration of sleep over a timeframe (e.g., from one week to the next).

Figure 8H:
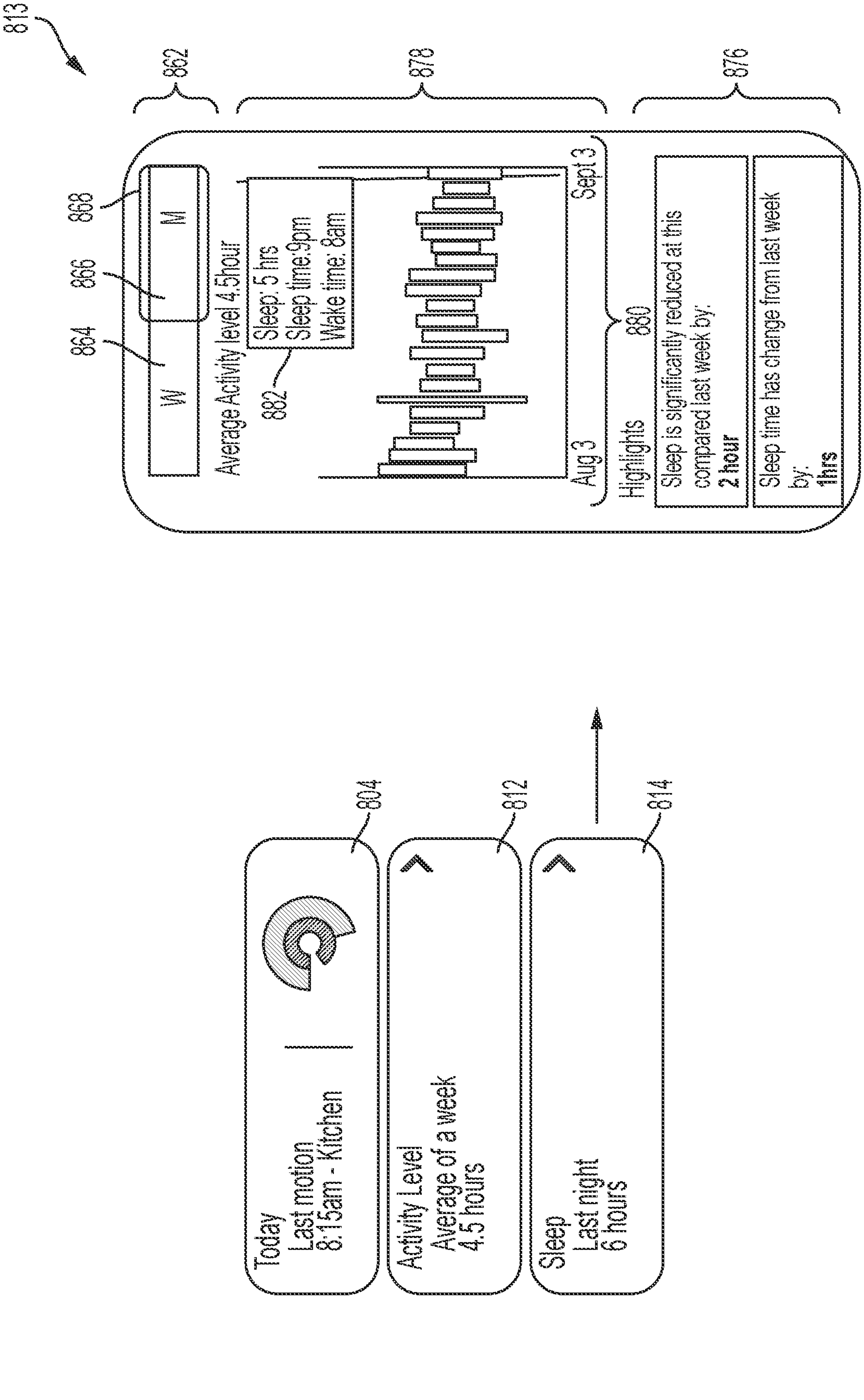

FIG. 8H shows an example graphical display 813 where the second tile 812 is selected by a user (e.g., by the user's finger touch on the user device's touch screen) and where the timeframe selected by the user is a month 866. In contrast to the graphical display 811 shown in FIG. 8G, the graphical display 813 includes an element 878 that includes a horizontal timeline that includes a time period 880 (including a series of time points) and a plot of sleep data indicating activity data related to sleep, for each time point in the time period 880. In the example shown in FIG. 8H, the timeframe selected is a month 866, and consequently, the time period 880 displayed is a one-month period. In some implementations, each time point in the time period 880 may represent a day within the one-month period. In some instances, the element 878 displays information 882 related to the activity data related to sleep in response to the user selecting the sleep data (e.g., by the user's finger touch on the user device's touch screen). For example, the information 874 may indicate a total duration of sleep observed for the selected time point (e.g., 5 hours in the example of FIG. 8G), a time at which sleep commenced for the selected time point (e.g., 9 pm in the example of FIG. 8G), and a time at which sleep concluded for the selected time point (e.g., 8 am in the example of FIG. 8G).

Figure 9A:
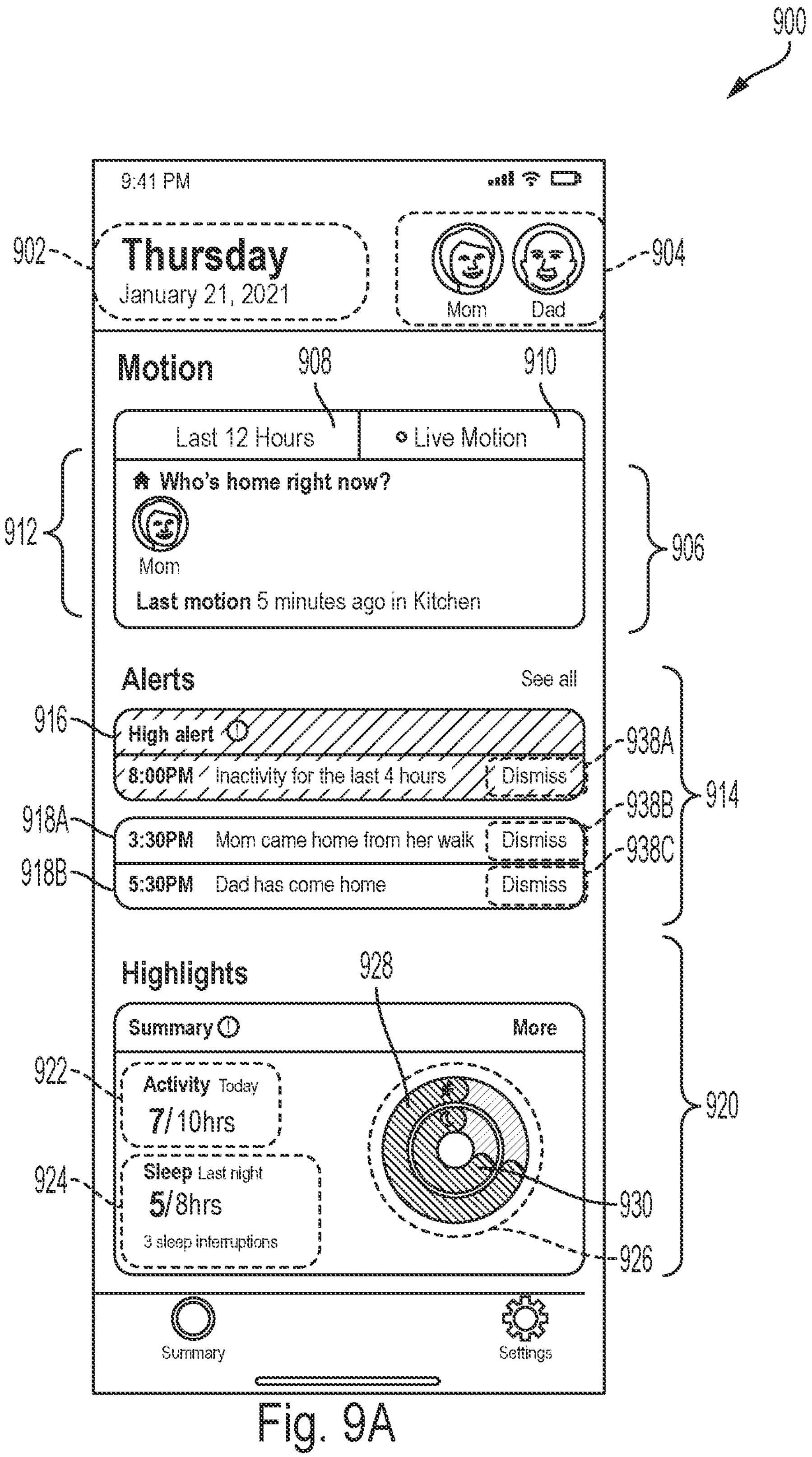
FIGS. 9A to 9F show examples of other graphical displays that may be generated by the system shown in FIG. 7.

FIGS. 9A to 9F show examples of other graphical displays that may be generated by the system 700 shown in FIG. 7. The graphical displays shown in FIGS. 9A to 9F can, as an example, be used in instances where motion and activity of one or more individuals are remotely monitored by a caregiver (e.g., a family member or a third-party caregiver). In FIG. 9A, the example graphical display 900 includes an element 902 that indicates the day and date corresponding to the motion and activity data. In some instances, the graphical display 900 also includes an element 904 that indicates the individual(s) whose motion and activity are being monitored. The graphical display 900 also includes element 906 that summarizes motion data for the indicated day and date 902. The graphical display 900 can also include tiles 908 and 910 that are selectable by the caregiver. In some instances, the tiles 908 and 910 allow the caregiver to display a summary of motion data for a historical time period (e.g., tile 908, which can be selected to show motion data for the last 12 hours) or a summary of live motion data (e.g., when tile 910 is selected). In the example shown in FIG. 9A, neither of the tiles 908 or 910 is selected, and the display 912 includes an indication of the individual who is currently in the space being monitored (e.g., mom is home right now) and an indication of when and where motion was last detected (e.g., motion was last detected 5 minutes ago in the kitchen). The graphical display 900 also includes element 914 that displays alerts to the caregiver. The alerts can be categorized into high priority alerts (e.g., shown in tile 916) and routine alerts (e.g., shown in tiles 918A, 918B). In some instances, high priority alerts are generated when no motion or activity was detected in the space for an extended period of time (e.g., inactivity for the last 4 hours). Each alert displayed by the element 914 can have an associated timestamp (e.g., 8:00 PM for tile 916, and 3:30 PM and 5:30 PM for tiles 918A, 918B, respectively). The graphical display 900 further includes element 920 that summarizes sleep and activity data for the indicated day and date 902. As an example, the element 920 can indicate the actual duration of activity relative to the targeted duration of movement (e.g., shown by element 922) and the actual duration of sleep relative to the targeted duration of sleep (e.g., shown by element 924). In some instances, the element 924 can also summarize the number of sleep interruptions that occurred while the individual being monitored was asleep. The element 920 can also include a chart 926 that displays (e.g., simultaneously displays) the duration of movement for the day (indicated by circular chart 928) and the duration of sleep for the day (indicated by circular chart 930).

Figure 9B:
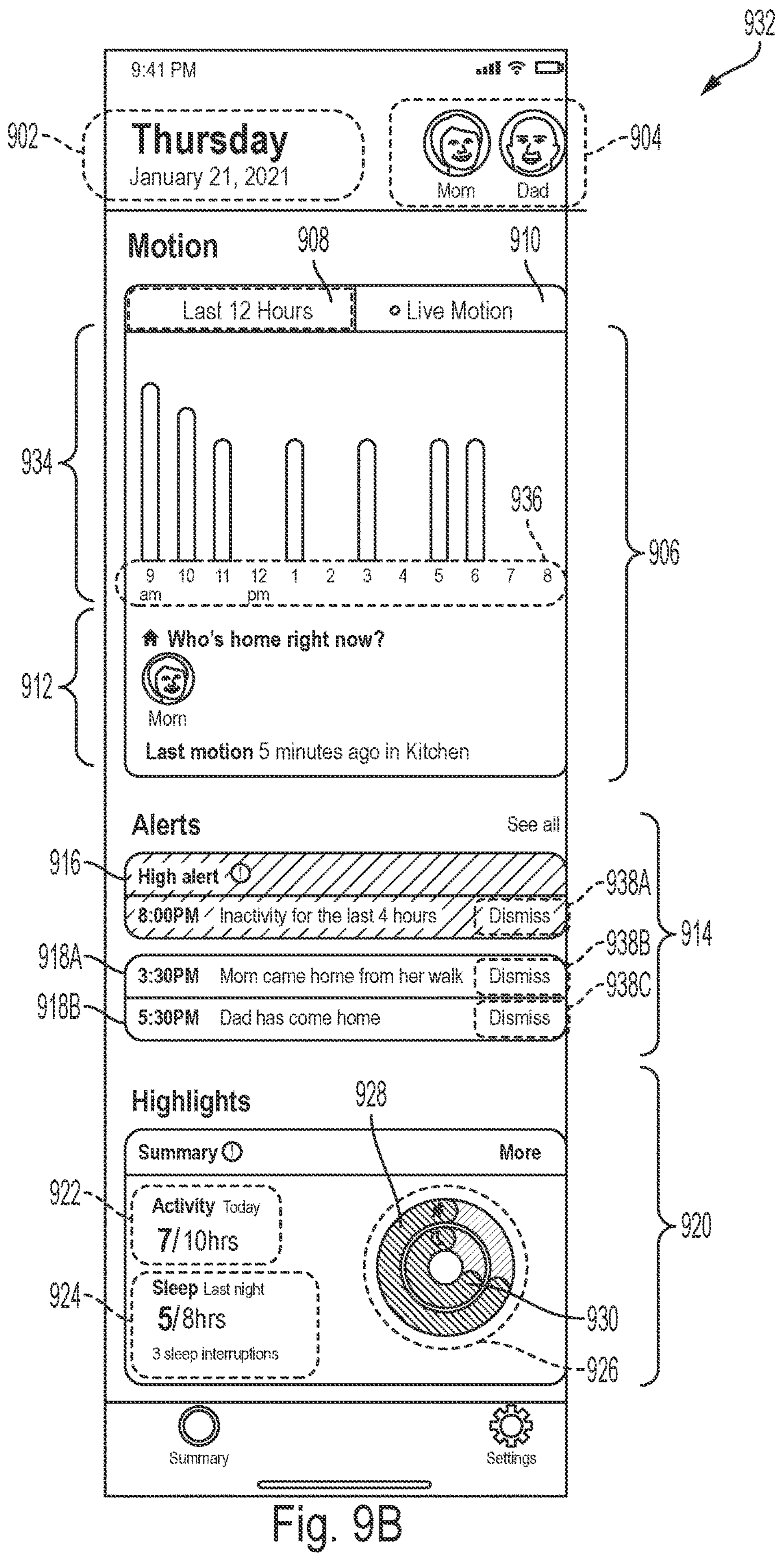
Figure 9C:
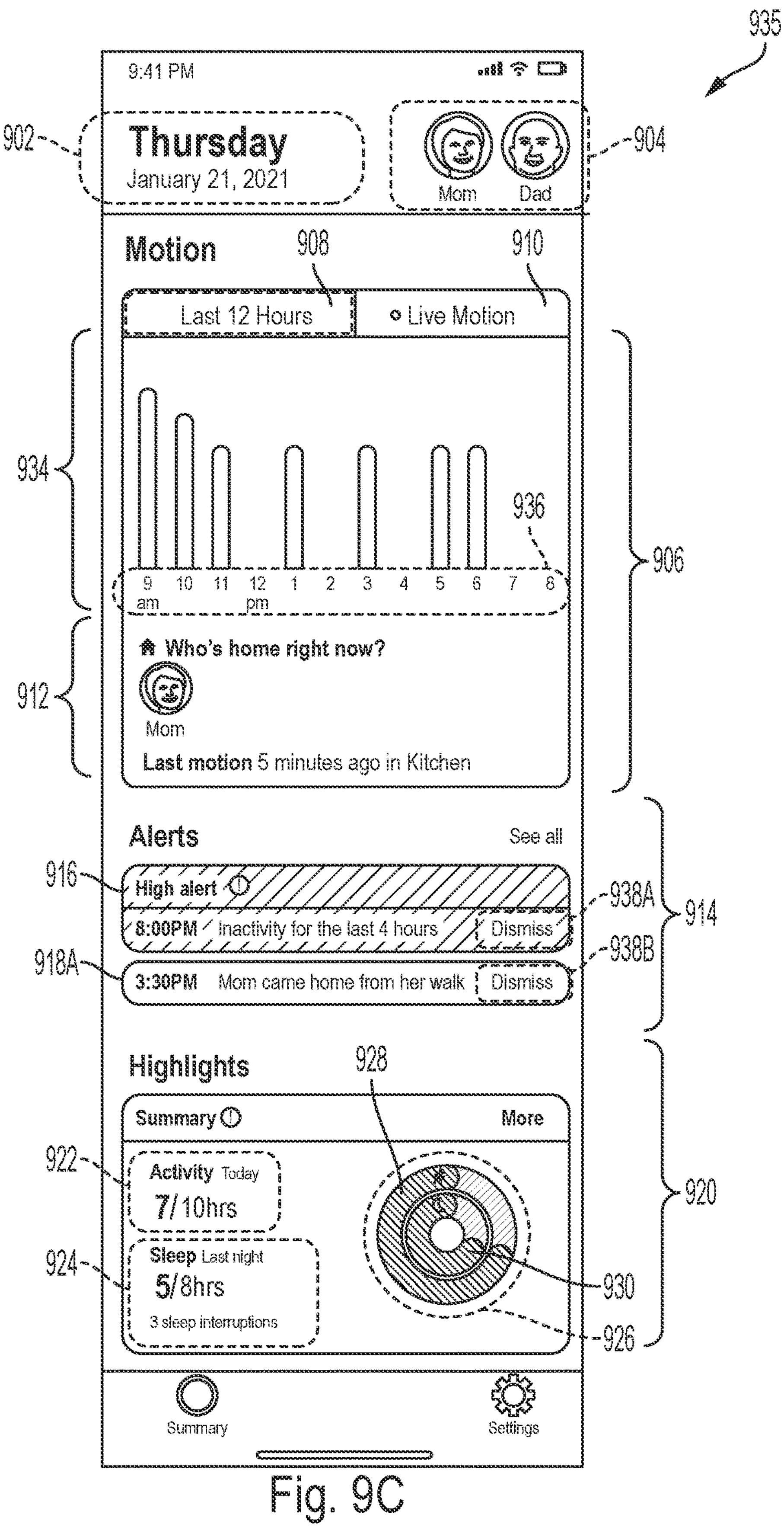
Figure 9D:
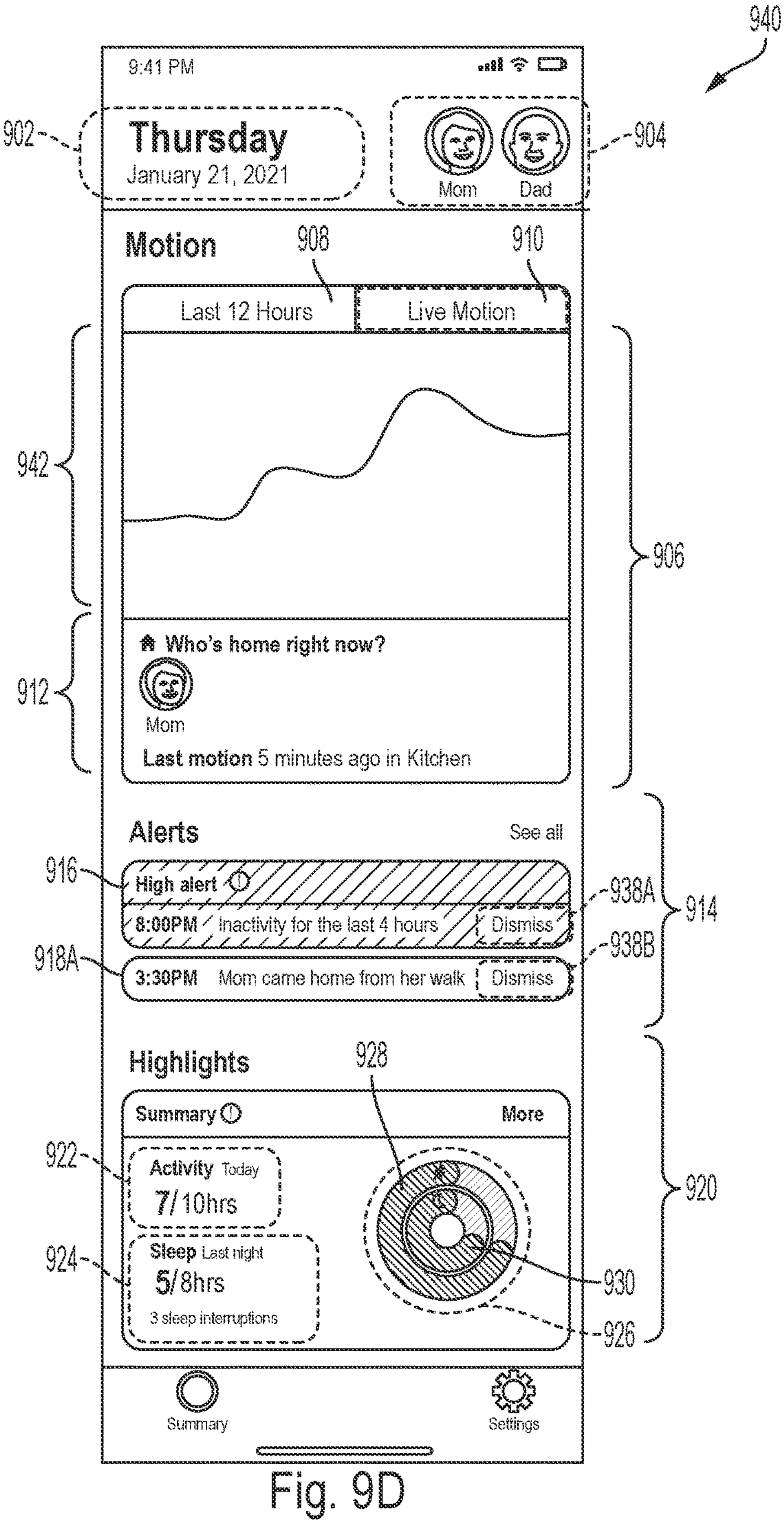

FIG. 9B shows an example graphical display 932 when tile 908 is selected and where the element 906 further includes a plot of motion data 934. The plot 934 includes a horizontal timeline that includes a time period 936 (including a series of time points) and a plot of motion data indicating a degree of motion detected by the motion detection system for each time point in the time period 936. The example plot 934 in FIG. 9B is shown as a bar chart; however, other types of graphs are possible in other examples, such as a line graph, a scatter plot, a histogram, etc. FIG. 9C shows an example graphical display 935 when tile 908 is selected and where an alert is dismissed by the user or caregiver. For example, the graphical displays shown in FIGS. 9A and 9B illustrate that each alert 916, 918A, 918B includes a respective selectable button 938A, 938B, 938C that allows the caregiver to dismiss the alert. In the example of FIG. 9C, the routine alert 918B has been dismissed by the caregiver. FIG. 9D shows an example graphical display 940 where the tile 910 is selected to show live motion data. In some instances, selection of the tile 910 can cause a plot 942 to be displayed. The plot 942 includes a horizontal timeline that represents a time period (e.g., in arbitrary units and scale) and a plot of motion data indicating a degree of motion detected by the motion detection system for each time point in the time period. The example plot 942 can be actively updated, adjusting as motion is detected, and relative to the degree of motion detected. The example plot 942 in FIG. 9D is shown as a line graph; however, other types of graphs are possible in other examples, such as a bar chart, a scatter plot, a histogram, etc.

Figure 9E:
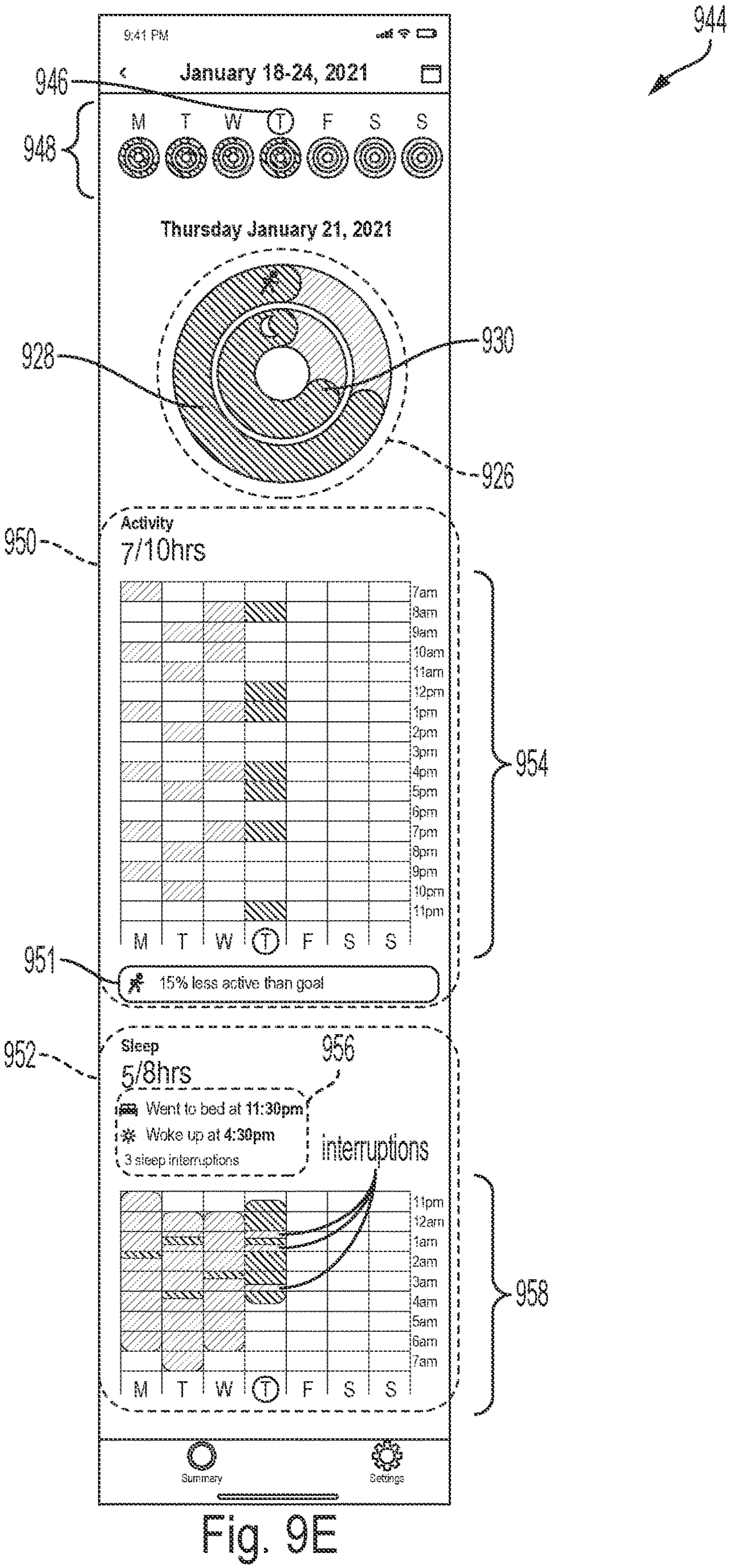

Each element 922 and 924 can be expanded to display further metrics of interest. FIG. 9E shows an example graphical display 944 where elements 922 and 924 are selected by a user (e.g., by the user's finger touch on the user device's touch screen). The graphical display 944 includes the chart 926 and an indication 946 of which day of a particular timeframe (e.g., a week in the example of FIG. 9E) the chart 926 corresponds to. The graphical display 944 also includes an element 948 that displays a summary of motion and sleep for each day of the week, where each day of the week has a respective chart that displays (e.g., simultaneously displays) the duration of movement for the respective day (indicated by the outer circular chart) and the duration of sleep for the respective day (indicated by the inner circular chart). For the day highlighted by the indication 946, the graphical display 944 also includes elements 950 and 952 that provide further details related to the day's chart 926. The element 950 can indicate the actual duration of movement observed for the day relative to the targeted duration of movement for the day (e.g., indicated as 7/10 hours in the example of FIG. 9E) and the times during the day when movement was detected (e.g., indicated by element 954). The element 950 can also include a comparison 951 of an actual value of interest and a benchmark value of interest (e.g., the example comparison 951 in FIG. 9E indicates that the individual was 15% less active than the benchmark activity level). The element 952 can indicate the actual duration of sleep observed relative to the targeted duration of sleep (e.g., indicated as 5/8 hours in the example of FIG. 9E), an element 956 that indicates the bedtime, the wake time, and the number of sleep disruptions detected, and an element 958 that indicates the times during which sleep disruptions were detected.

Figure 9F:
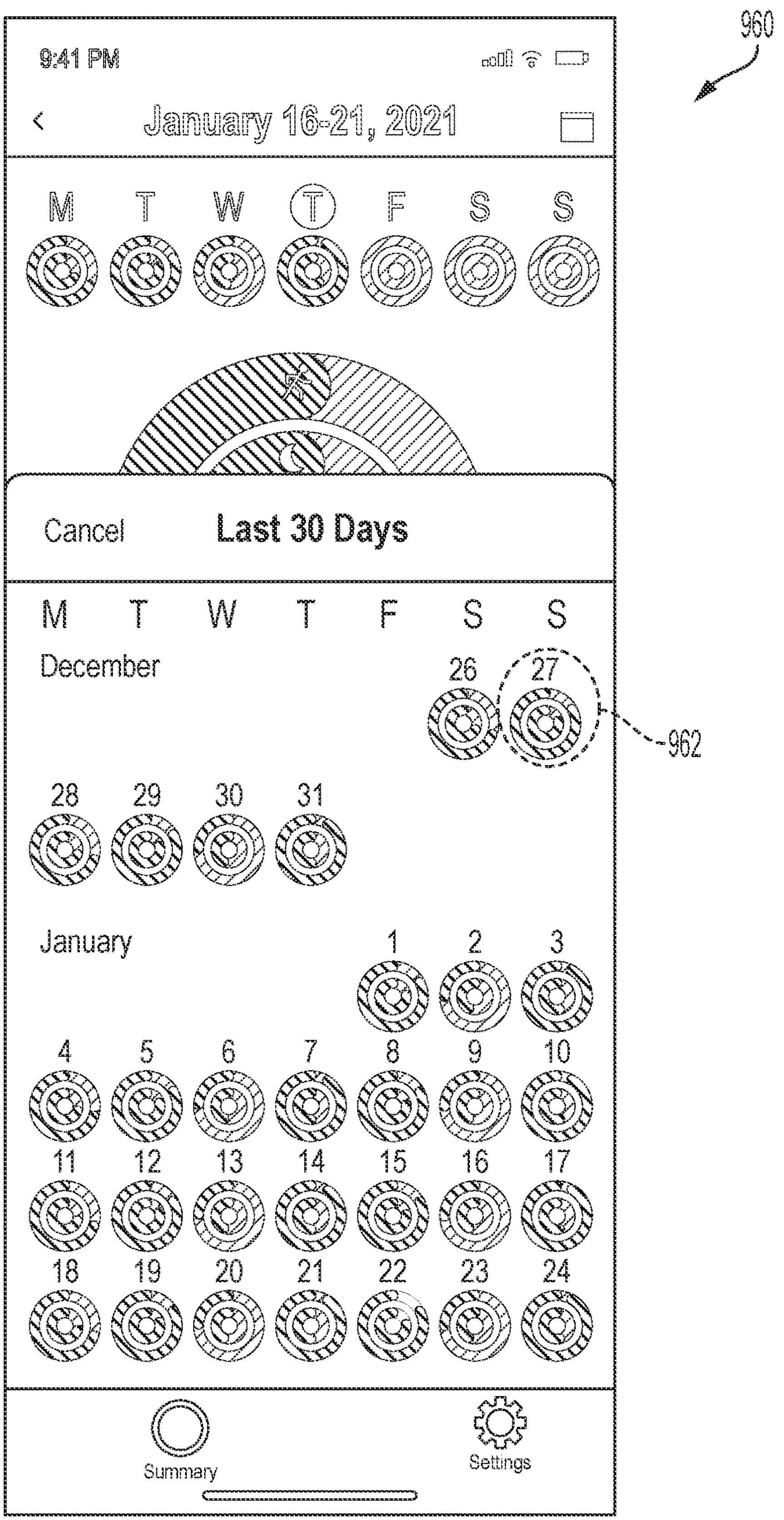

The timeframes indicated by example graphical displays shown in FIGS. 9A to 9E are not limited to a day, a week, or a month, and can be any time period (e.g., based on a choice by the user, which can be informed by user input data 524). FIG. 9F shows an example graphical display 960 that summarizes motion and sleep data over the last 30 days, where the motion and sleep data for each day is illustrated by a respective chart 962 that displays (e.g., simultaneously displays) the duration of movement for the day (indicated by an outer circular chart) and the duration of sleep for the day (indicated by an inner circular chart).

Figure 10:
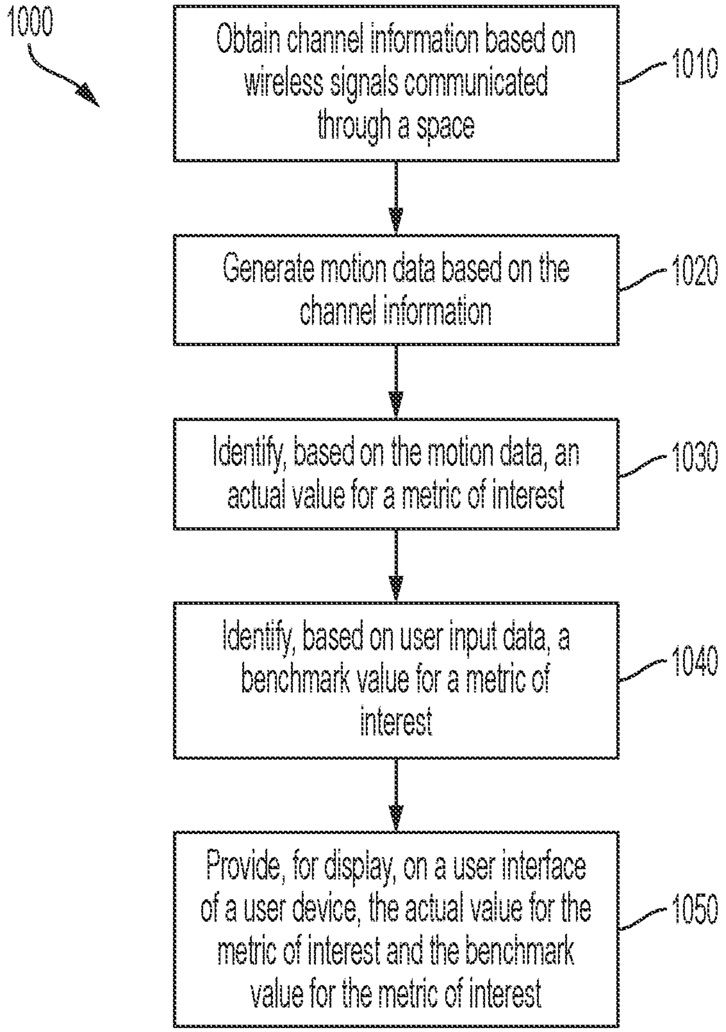
FIG. 10 is a flow chart showing an example process for generating actual and benchmark values for one or more metrics of interest.

FIG. 10 is a flowchart showing an example process 1000 performed, for example, by a motion detection system (e.g., the motion detection system 504 shown in FIG. 5). In the example process 1000, the motion detection system generates actual and benchmark values for one or more metrics of interest. The motion detection system can process information based on wireless signals transmitted (e.g., on wireless links between wireless communication devices) through a space to detect motion of objects in the space (e.g., as described with respect to FIG. 1, 2A, 2B, 2C, or otherwise). Operations of the process 1000 may be performed by a remote computer system (e.g., a server in the cloud), a wireless communication device (e.g., one or more of the wireless communication devices), or another type of system. For example, operations in the example process 1000 may be performed by one or more of the example wireless communication devices 102A, 102B, 102C in FIG. 1, one or more of the example wireless communication devices 204A, 204B, 204C in FIGS. 2A and 2B, or one or more of the client devices 232 and APs 226, 228 in FIG. 2C.

The example process 1000 may include additional or different operations, and the operations may be performed in the order shown or in another order. In some cases, one or more of the operations shown in FIG. 10 can be implemented as processes that include multiple operations, sub-processes or other types of routines. In some cases, operations can be combined, performed in another order, performed in parallel, iterated, or otherwise repeated or performed in another manner.

At 1010, channel information is obtained based on wireless signals communicated through a space. The space (e.g., the space 201 shown in FIG. 2C) may include multiple locations (e.g., the locations 250,252, 254, 256 shown in FIG. 2C), and the wireless signals may be communicated over a time period by a wireless communication network having multiple wireless communication devices (e.g., the devices 232, 226, 228 shown in FIG. 2C).

At 1020, motion data is generated based on the channel information. As discussed above in reference to FIG. 5, the motion data can include motion indicator values, $m_t$, indicative of a degree of motion that occurred in the space for each time point t in the series of time points within the time period. Additionally, the motion data can include motion localization values $[L_{t,1}\ L_{t,2}\ \ldots\ L_{t,N}]$ for the multiple locations in the space (where N is the number of locations in the space). The motion localization value for each individual location represents a relative degree of motion detected at the individual location.

At 1030, an actual value for a metric of interest for the time period is identified based on the motion data. As discussed above, the metric of interest can include one or more of the following: the degree of motion that occurred in the space within the time interval; the degree of motion that occurred at each of the N locations in the space within the time interval $[t_0, t_p]$; the average degree of motion that occurred at each of the N locations in the space within the time interval $[t_0, t_p]$; a determination of which location, among the N locations in the space, experienced the largest degree of motion within the time interval $[t_0, t_p]$; or a determination of the number of active minutes at each of the N locations within the time interval $[t_0, t_p]$. In some implementations, the metric of interest can include sleep data, and the actual value of the metric of interest can include one or more of the following: a total duration of sleep observed during a time interval $[t_{s1}, t_{s2}]$; a total duration of movement observed during the time interval $[t_{s1}, t_{s2}]$; a degree of motion observed for each time point within the time interval $[t_{s1}, t_{s2}]$; or sleep levels observed during the time interval $[t_{s1}, t_{s2}]$. In some implementations, the metric of interest can include movement data, and the actual value of the metric of interest can include one or more of the following: a total duration of movement observed during the time interval $[t_{a1}, t_{a2}]$; a degree of motion observed at each location for each time point within the time interval $[t_{a1}, t_{a2}]$; or the location exhibiting the highest degree of motion during the time interval $[t_{a1}, t_{a2}]$.

At 1040, a benchmark value for the metric of interest is identified based on user input data (e.g., user input data 524 shown in FIG. 5). As discussed above, the user input data can include a first time interval during which a person expects to be asleep, a targeted duration of sleep during the first time interval, a second time interval during which a person expects to be awake, a targeted duration of movement during the second time interval, or an indication of a time duration during which motion is not expected, although other user input data can be used in other examples.

At 1050, the actual value for the metric of interest and the benchmark value for the metric of interest are provided for display on a user interface of a user device. For example, the values may be displayed as shown in FIGS. 8A-8H, FIGS. 9A-9F, or they may be displayed in another manner (e.g., as a bar chart, a line graph, a scatter plot, a histogram, etc.).

Figure 11:
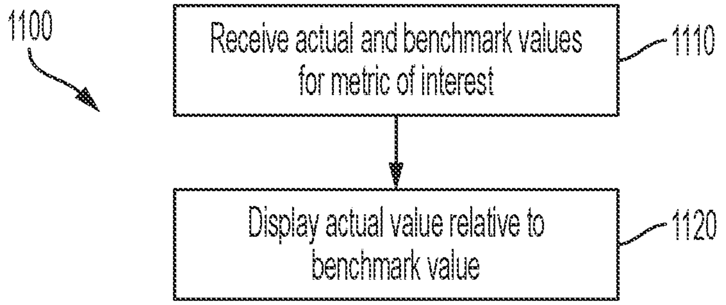
FIG. 11 is a flow chart showing an example process for generating a graphical display based on the actual and benchmark values generated in FIG. 10.

FIG. 11 is a flowchart showing an example process 1100 performed, for example, by a system for generating a graphical display (e.g., the system 700 shown in FIG. 7). Operations of the process 1100 may be performed by a remote computer system (e.g., a server in the cloud), a wireless communication device (e.g., one or more of the wireless communication devices), or another type of system. For example, operations in the example process 1100 may be performed by one or more of the example wireless communication devices 102A, 102B, 102C in FIG. 1, one or more of the example wireless communication devices 204A, 204B, 204C in FIGS. 2A and 2B, or one or more of the client devices 232 and APs 226, 228 in FIG. 2C.

The example process 1100 may include additional or different operations, and the operations may be performed in the order shown or in another order. In some cases, one or more of the operations shown in FIG. 11 can be implemented as processes that include multiple operations, sub-processes or other types of routines. In some cases, operations can be combined, performed in another order, performed in parallel, iterated, or otherwise repeated or performed in another manner.

At 1110, the actual value for the metric of interest and the benchmark value for the metric of interest (e.g., that are provided at 1050 in FIG. 10) are received. At 1120, the actual value for the metric of interest is displayed relative to the benchmark value for the metric of interest. In some instances, the actual value for the metric of interest and the benchmark value for the metric of interest are displayed using a graphical display, examples of which are discussed in FIGS. 8A to 8H and FIGS. 9A to 9F.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer storage medium for execution by, or to control the operation of, data-processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

Some of the operations described in this specification can be implemented as operations performed by a data processing apparatus on data stored on one or more computer-readable storage devices or received from other sources.

The term "data-processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

In a general aspect, metrics of interest are generated based on motion data and displayed (e.g., on a user interface).

In a first example, a method includes obtaining channel information based on wireless signals communicated through a space over a time period by a wireless communication network. The wireless communication network includes a plurality of wireless communication devices, and the space includes a plurality of locations. The method includes generating motion data based on the channel information. The motion data includes motion indicator values and motion localization values for the plurality of locations. The motion indicator values may be indicative of a degree of motion that occurred in the space for each time point in a series of time points within the time period. The motion localization value for each individual location may represent a relative degree of motion detected at the individual location for each time point in the series of time points within the time period. The method further includes identifying, based on the motion data, an actual value for a metric of interest for the time period; identifying, based on user input data, a benchmark value for the metric of interest for the time period; and providing, for display on a user interface of a user device, the actual value for the metric of interest and the benchmark value for the metric of interest.

Implementations of the first example may include one or more of the following features. The user input data may include a first time interval within the time period, the first time interval indicative of a time interval during which a person expects to be asleep; and a targeted duration of sleep during the first time interval. The actual value of the metric of interest may include at least one of: a total duration of sleep observed during the first time interval; a total duration of movement observed during the first time interval; a degree of motion observed for each time point within the first time interval; or sleep levels observed during the first time interval. The sleep levels observed during the first time interval may include: durations of restful sleep within the first time interval; durations of light sleep within the first time interval; and durations of disrupted sleep within the first time interval. The user input data may include a second time interval within the time period, the second time interval indicative of times during which a person expects to be awake; and a targeted duration of movement during the second time interval. The actual value of the metric of interest may include at least one of: a total duration of movement observed during the second time interval; a degree of motion observed at each location for each time point within the second time interval; or the location exhibiting the highest degree of motion during the second time interval. The user input data may include an indication of a time duration within the time period during which motion is not expected, and the method may further include: determining, based on the user input data and the motion data, that motion has occurred during the time duration; and providing, for display on the user interface of the user device, a notification that motion has occurred within the time duration during which motion is not expected. The user input data may include an indication of one or more locations at which motion is not expected, and the method may further include: determining, based on the user input data and the motion data, that motion has occurred at the one or more locations; and providing, for display on the user interface of the user device, a notification that motion has occurred at one or more of the locations at which motion is not expected. Each wireless communication device may be located in a respective location of the plurality of locations. The wireless signals communicated through the space may include wireless signals exchanged on wireless communication links in the wireless communication network, and each motion indicator value represents the degree of motion detected from the wireless signals exchanged on a respective one of the wireless communication links.

In a second example, a method may include receiving an actual value for a metric of interest for a time period. The actual value for the metric of interest may be identified based on motion data, and the motion data may be generated based on channel information. The channel information may be obtained based on wireless signals communicated through a space over the time period by a wireless communication network. The wireless communication network may include a plurality of wireless communication devices, and the space may include a plurality of locations. The motion data includes motion indicator values and motion localization values for the plurality of locations. The motion indicator values may be indicative of a degree of motion that occurred in the space for each time point in a series of time points within the time period. The motion localization value for each individual location may represent a relative degree of motion detected at the individual location for each time point in the series of time points within the time period. The method further includes receiving a benchmark value for the metric of interest for the time period. The benchmark value for the metric of interest may be identified based on user input data. The method additionally includes displaying, on a user interface of a user device, the actual value for the metric of interest relative to the benchmark value for the metric of interest.

Implementations of the first example may include one or more of the following features. The method may additionally include generating a notification in response to the actual value of the metric of interest being greater than or equal to the benchmark value of the metric of interest.

In a third example, a non-transitory computer-readable medium stores instructions that are operable when executed by data processing apparatus to perform one or more operations of the first or second examples. In a fourth example, a system includes a plurality of wireless communication devices, and a computer device configured to perform one or more operations of the first or second examples.

Implementations of the fourth example may include one or more of the following features. One of the wireless communication devices can be or include the computer device. The computer device can be located remote from the wireless communication devices.

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of embodiments have been described. Nevertheless, it will be understood that various modifications can be made. Accordingly, other embodiments are within the scope of the following claims.

What is claimed is:

1. A method of operating a motion detection system, the method comprising:

by operation of one or more communication interfaces, receiving radio frequency wireless signals communicated through a space over a time period by a plurality of wireless communication devices, the space comprising a plurality of locations;

processing the radio frequency wireless signals to generate channel information;

by operation of a motion detection engine of a motion detection system, generating motion data based on the channel information, the motion data comprising a series of vectors in a series of time points within the time period, the motion data comprising:

motion indicator values indicative of a degree of motion that occurred in the space for each time point in the series of time points within the time period; and motion localization values for the plurality of locations, the motion localization value for each individual location representing a relative degree of motion detected at the individual location for each time point in the series of time points within the time period;

by operation of a pattern extraction engine of the motion detection system, processing the series of vectors to generate output data for the time period, wherein processing the series of vectors comprises:

determining an aggregate degree of motion that occurred at each of the individual locations during the time period; and determining a duration of activity that occurred at each of the individual locations during the time period, wherein determining the duration of activity at each individual location comprises processing the motion localization values for that individual location across the series of time points to identify time points within the time period during which the motion localization value for the individual location is non-zero; and based on the output data generated by the pattern extraction engine, sending a notification from the motion detection system for processing by an external system.

2. The method of claim 1, wherein generating the channel information comprises generating a set of channel responses that characterize communication paths between wireless transmitters and wireless receivers in a wireless communication network.

3. The method of claim 1, wherein generating the channel information comprises generating beamforming state information based on a wireless beamforming system.

4. The method of claim 1, wherein receiving radio frequency wireless signals comprises receiving radio frequency wireless signals that are formatted according to a wireless communication standard for communication in a wireless communication network.

5. A non-transitory computer-readable medium comprising instructions that are operable, when executed by a data-processing apparatus, to perform operations comprising:

generating channel information by processing radio frequency wireless signals that were communicated through a space over a time period by a plurality of wireless communication devices, the space comprising a plurality of locations;

by operation of a motion detection engine of a motion detection system, generating motion data based on the channel information, the motion data comprising a series of vectors in a series of time points within the time period, the motion data comprising:

motion indicator values indicative of a degree of motion that occurred in the space for each time point in the series of time points within the time period; and motion localization values for the plurality of locations, the motion localization value for each individual location representing a relative degree of motion detected at the individual location for each time point in the series of time points within the time period;

by operation of a pattern extraction engine of the motion detection system, processing the series of vectors to generate output data for the time period, wherein processing the series of vectors comprises:

determining an aggregate degree of motion that occurred at each of the individual locations during the time period; and determining a duration of activity that occurred at each of the individual locations during the time period, wherein determining the duration of activity at each individual location comprises processing the motion localization values for that individual location across the series of time points to identify time points within the time period during which the motion localization value for the individual location is non-zero; and based on the output data generated by the pattern extraction engine, sending a notification from the motion detection system for processing by an external system.

6. The non-transitory computer-readable medium of claim 5, wherein generating the channel information comprises generating a set of channel responses that characterize communication paths between wireless transmitters and wireless receivers in a wireless communication network.

7. The non-transitory computer-readable medium of claim 5, wherein generating the channel information comprises generating beamforming state information based on a wireless beamforming system.

8. The non-transitory computer-readable medium of claim 5, wherein the radio frequency wireless signals comprise radio frequency wireless signals that are formatted according to a wireless communication standard for communication in a wireless communication network.

9. A system comprising:

a plurality of wireless communication devices;

a computer system comprising one or more processors configured to perform operations comprising:

generating channel information by processing radio frequency wireless signals that were communicated through a space over a time period by the plurality of wireless communication devices, the space comprising a plurality of locations;

by operation of a motion detection engine, generating motion data based on the channel information, the motion data comprising a series of vectors in a series of time points within the time period, the motion data comprising:

motion indicator values indicative of a degree of motion that occurred in the space for each time point in the series of time points within the time period; and motion localization values for the plurality of locations, the motion localization value for each individual location representing a relative degree of motion detected at the individual location for each time point in the series of time points within the time period;

by operation of a pattern extraction engine, processing the series of vectors to generate output data for the time period, wherein processing the series of vectors comprises:

determining an aggregate degree of motion that occurred at each of the individual locations during the time period; and determining a duration of activity that occurred at each of the individual locations during the time period, wherein determining the duration of activity at each individual location comprises processing the motion localization values for that individual location across the series of time points to identify time points within the time period during which the motion localization value for the individual location is non-zero; and based on the output data generated by the pattern extraction engine, sending a notification from the motion detection system for processing by an external system.

10. The system of claim 9, wherein generating the channel information comprises generating a set of channel responses that characterize communication paths between wireless transmitters and wireless receivers in a wireless communication network.

11. The system of claim 9, wherein generating the channel information comprises generating beamforming state information based on a wireless beamforming system.

12. The system of claim 9, wherein the radio frequency wireless signals comprises radio frequency wireless signals that are formatted according to a wireless communication standard for communication in a wireless communication network.

* * * * *